(12) United States Patent
Kaminishi et al.

(10) Patent No.: US 8,481,711 B2
(45) Date of Patent: Jul. 9, 2013

(54) NEURITE OUTGROWTH AGENT

(75) Inventors: Hidenori Kaminishi, Fukuoka (JP); Junei Kinjo, Fukuoka (JP); Ryota Tsuchihashi, Fukuoka (JP); Tsuyoshi Ikeda, Kumamoto (JP); Akihiro Sakamoto, Kagoshima (JP)

(73) Assignee: Hidenori Kamanishi, Fukuoka (JP)

( * ) Notice: Subject to any disclaimer, the term of this patent is extended or adjusted under 35 U.S.C. 154(b) by 0 days.

(21) Appl. No.: 13/806,933

(22) PCT Filed: Apr. 20, 2011

(86) PCT No.: PCT/JP2011/002319
§ 371 (c)(1),
(2), (4) Date: Dec. 26, 2012

(87) PCT Pub. No.: WO2012/004917
PCT Pub. Date: Jan. 12, 2012

(65) Prior Publication Data
US 2013/0102771 A1 Apr. 25, 2013

(30) Foreign Application Priority Data

Jul. 6, 2010 (JP) ................................. 2010-154279

(51) Int. Cl.
*C07H 21/00* (2006.01)
(52) U.S. Cl.
USPC ........................................................ 536/25.6
(58) Field of Classification Search
None
See application file for complete search history.

(56) References Cited

FOREIGN PATENT DOCUMENTS

| | | |
|---|---|---|
| JP | 08-507307 A | 8/1996 |
| JP | 08-231501 A | 9/1996 |
| JP | 10-507772 A | 7/1998 |
| JP | 11-310602 | 11/1999 |
| JP | 2001-515916 A | 9/2001 |
| JP | 2001-524936 A | 12/2001 |
| JP | 2002-060340 A | 2/2002 |
| JP | 2003-514893 A | 4/2003 |
| JP | 2006-052192 A | 2/2006 |
| JP | 2007022966 A | 2/2007 |
| JP | 2007-230945 A | 9/2007 |
| JP | 2007-230946 A | 9/2007 |
| JP | 2008-007446 A | 1/2008 |
| JP | 2008-501343 A | 1/2008 |
| JP | 2008-100954 A | 5/2008 |
| JP | 2009-132622 A | 6/2009 |
| WO | WO 94/20515 A | 9/1994 |
| WO | WO 96/13512 A2 | 5/1996 |
| WO | WO 98/16184 A2 | 4/1998 |
| WO | WO 99/12951 A1 | 3/1999 |
| WO | WO 01/38304 A1 | 5/2001 |
| WO | WO 2005/097155 A1 | 10/2005 |
| WO | WO 2005/103089 A1 | 11/2005 |
| WO | WO 2006/001982 A2 | 1/2006 |
| WO | WO 2010/022244 A1 | 2/2010 |

OTHER PUBLICATIONS

Jeck et al., "Interaction Between Dehydrogenases and a New NAD-Isomer", Journal of Biosciences, 1975, 734-738.*
Jeck et al., "Interaction between Dehydrogenases and a New NAD®-Isomer," Journal of Biosciences, 1975, 734-738.
Tanimori et al., "An Efficient Chemical Synthesis of Nicotinamide Riboside (NAR) and Analogues," Bioorganic & Medicinal Chemistry Letters, 2002, 12:1135-1137.

* cited by examiner

*Primary Examiner* — Traviss C McIntosh, III
(74) *Attorney, Agent, or Firm* — Foley & Lardner LLP

(57) ABSTRACT

An object of the present invention is to provide a non-peptidic nerve axon and/or neurite outgrowth agent for allowing a nerve axon and a neurite to elongate. 3-(Aminocarbonyl)-1-[5-O-[[1-(6-amino-9H-purin-9-yl)-1-deoxy-β-D-ribofuranos-5-O-yl]phosphonyloxy(oxylato)phosphinyl]-β-L-ribofuranosyl]pyridinium that is an analogue of nicotinamide adenine dinucleotide (NAD) comprising β-L-ribose as the sugar component is used as a nerve axon and/or neurite outgrowth agent or composition, a cancer cell growth suppressing and/or apoptosis inducing agent, or a cancer cell growth suppressing and/or apoptosis inducing composition.

1 Claim, 16 Drawing Sheets

1: ———— : β NAD
2: ———— : α NAD
3: ———— : SYNTHETIC PREPARATION

Figure 5
(a)
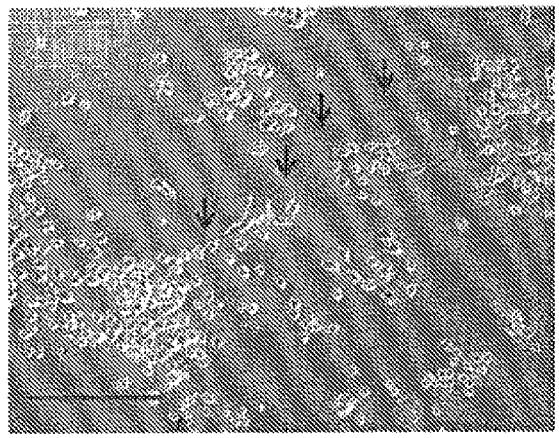
(b)
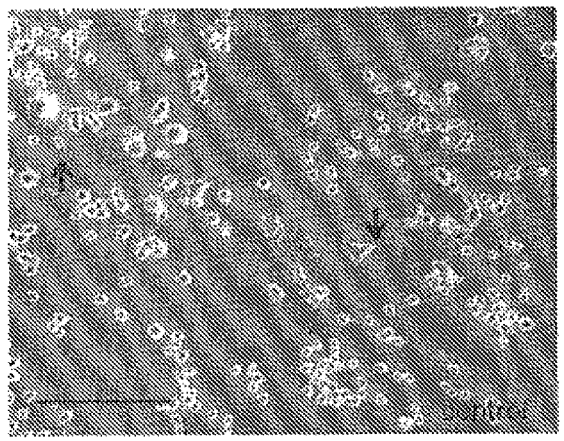
bar : 500 μm
Figure 6
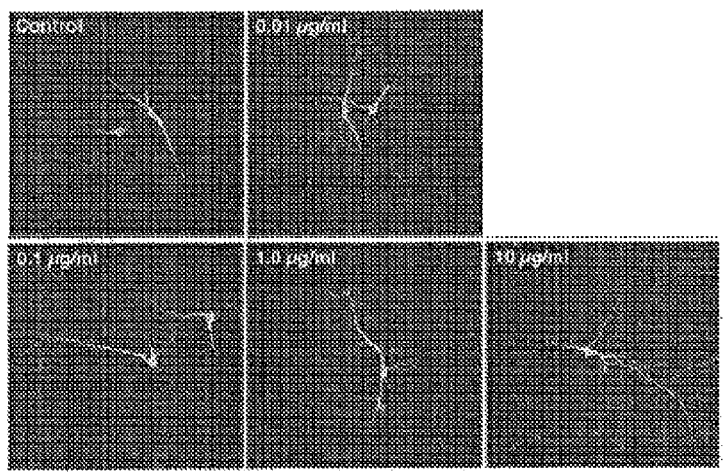

EFFECT OF ALLOWING NEURITES TO ELONGATE FROM FETAL RAT
BRAIN DOPAMINERGIC CELLS

NAD ANALOGUE OF THE PRESENT INVENTION (μg/ml)

Figure 16

EFFECT OF NAD ANALOGUE OF THE PRESENT INVENTION TO ALLOW NEURITES TO ELONGATE FROM HUMAN NEUROBLASTOMA-DERIVED CELLS (NB-1 CELLS) (MAGNIFICATION: 200 TIMES)

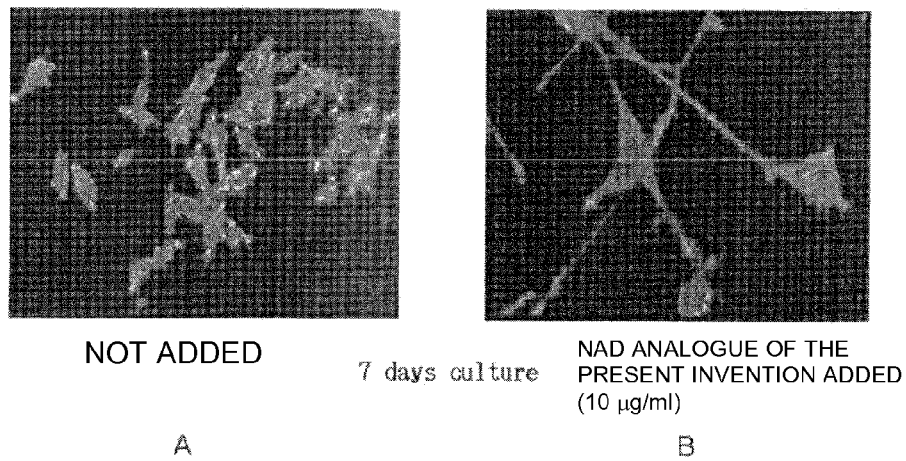

NOT ADDED 7 days culture NAD ANALOGUE OF THE PRESENT INVENTION ADDED (10 μg/ml)

EFFECT OF NAD ANALOGUE OF THE PRESENT INVENTION TO SUPPRESS GROWTH OF HUMAN MYELOID LEUKEMIA CELLS (HL-60 CELLS)

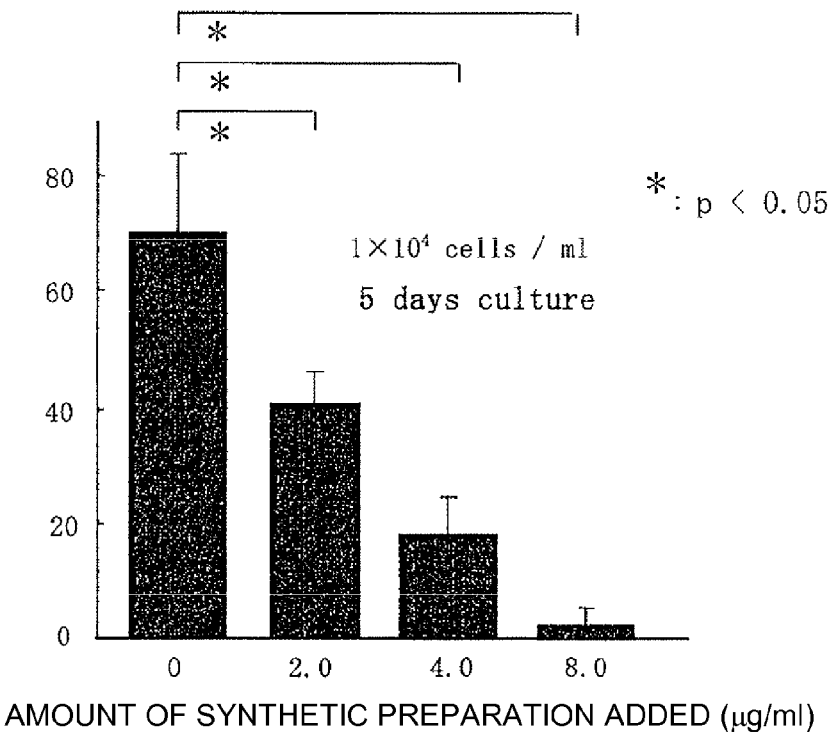

$*: p < 0.05$ $1 \times 10^4$ cells / ml
5 days culture

AMOUNT OF SYNTHETIC PREPARATION ADDED (μg/ml)

INDUCTION OF HUMAN MYELOID LEUKEMIA CELLS (HL-60 CELLS) TO APOPTOSIS BY NAD ANALOGUE OF THE PRESENT INVENTION

EFFECT OF NAD ANALOGUE OF THE PRESENT INVENTION TO SUPPRESS GROWTH OF RETINOIC ACID-RESISTANT LEUKEMIA CELLS (UF-1 CELLS)

AMOUNT OF NAD ANALOGUE OF THE PRESENT INVENTION ADDED (μg/ml)

EFFECT OF NAD ANALOGUE OF THE PRESENT INVENTION TO SUPPRESS GROWTH OF HUMAN COLON-ADENOCARCINOMA CELLS (HT29 CELLS)

AMOUNT OF NAD ANALOGUE OF THE PRESENT INVENTION ADDED (μg/ml)

NEURITE OUTGROWTH AGENT

CROSS-REFERENCE TO RELATED APPLICATIONS

This application is a National Stage application of PCT/JP2011/002319, filed Apr. 20, 2011, which claims priority from Japanese application JP 2010-154279, filed Jul. 6, 2010.

TECHNICAL FIELD

The present invention relates to a nerve axon and/or neurite outgrowth agent and an anticancer agent. More specifically, the present invention relates to: a nerve axon and/or neurite outgrowth agent and a cancer cell growth suppressing and/or apoptosis inducing agent, each of which comprises, as an active ingredient, a nicotinamide adenine dinucleotide (NAD) analogue in which the sugar component of the nicotinamide mononucleotide portion thereof is β-L-ribose; and food and a food material comprising the nicotinamide adenine dinucleotide (NAD) analogue, which are used for the functional recovery of cranial nerve or the prevention and/or treatment of cancer.

BACKGROUND ART

Once a neural circuit network is damaged by brain injury or spinal cord injury and the network is thereby cut off or results in nerve cell death, the physiological and/or motor functions governed by nerves are lost, and it becomes extremely difficult to restore the neural circuit. However, in order to recover and/or restore various lost functions, the reconstruction of networks among surviving nerve cells is essential, and thus, nerve axons extending from the surviving nerve cells and neurites extending from the nerve axons need to be regenerated. As a substance having an action to allow neurites to elongate, a nerve growth factor (NGF) secreted from nerve cells has attracted attention. NGF is a factor important and necessary for the growth and functional maintenance of nervous tissues. NGF is essential for the maturation and differentiation of sensory and sympathetic nerves in peripheral nerves, and has an action to prevent the degeneration of nerve cells upon brain injury. However, since NGF does not have blood-brain barrier (BBB) permeability, it is said that NGF cannot shift into brain from the periphery or via oral administration.

Conventionally, as non-peptidic neurite outgrowth agents, neurite outgrowth inducers, and neurite outgrowth promoters, the following non-peptidic agents have been known: a neurotrophic factor, which contains a 5-acyl-2-amino-1,3-selenazole analogue and which has a promoting action on the outgrowth of neurites from nerve cells (see patent document 1); a neurotrophic factor, which contains ebselen having a promoting action on the phosphorylation of mitogen-activated protein kinase (ERK1/2) of nerve cells and has a promoting action on the outgrowth of neurites from nerve cells (see patent document 2); a neurite outgrowth agent containing, as an active ingredient, at least one compound selected from the group consisting of coffeic acid and a derivative thereof (see patent document 3); a neurite outgrowth agent containing, as an active ingredient, at least one plant extract selected from the group consisting of rosemary and sage that contain carnosic acid (see patent document 4); a cell death suppressing substance containing lysophosphatidylethanolamine having an action to allow neurites to elongate from nerve cells (see patent document 5); a neurite outgrowth composition, which contains, as a main ingredient, a cell organelle alkalinization agent such as monensin or concanamycin A, and which acts to allow neurites to elongate from motor nerve cells, (see patent document 6); a neurite outgrowth agent containing polyalkoxyflavonoid such as nobiletin or tangeretin (see patent document 7); a neurite outgrowth activator containing a glycosaminoglycan derivative (see patent document 8); a neurite outgrowth agent containing a lactacystin derivative (see patent document 9); a neurite outgrowth agent containing a small molecule heterocyclic ketone or thioester compound (see patent document 10); a neurite outgrowth agent containing derivatives of ganglioside and N-acyl-N-lyso-ganglioside, N'-acyl-N'-lyso-ganglioside, and N,N'-di- or poly-acyl-N,N'-dilyso-ganglioside, in which at least one hydroxyl group of saccharide, sialic acid, and a ceramide residue, except for persulfated derivatives in the hydroxyl, sialic acid and ceramide group of $GM_1$, $GD_{1a}$, $GD_{1b}$ and $GT_{1b}$ gangliosides (see patent document 11); a neurite outgrowth agent comprising a chondroitin sulfate/dermatan sulfate hybrid chain containing a disaccharide of GlcUA(2S)-GalNAc(4S) (B unit) (see patent document 12); a neurite outgrowth inducer containing a sugar chain having a bisecting GlcNAc, a complex carbohydrate having the aforementioned sugar chain in the structure thereof, a derivative of the aforementioned sugar chain, etc. (see patent document 13); and a neurite outgrowth inducer containing, as an active ingredient, a low-molecular-weight synthetic compound (see patent document 14).

PRIOR ART DOCUMENTS

Patent Documents

Patent Document 1: Japanese unexamined Patent Application Publication No. 2008-100954
Patent Document 2: Japanese unexamined Patent Application Publication No. 2008-7446
Patent Document 3: Japanese unexamined Patent Application Publication No. 2007-230946
Patent Document 4: Japanese unexamined Patent Application Publication No. 2007-230945
Patent Document 5: Japanese unexamined Patent Application Publication No. 2007-22966
Patent Document 6: Japanese unexamined Patent Application Publication No. 2006-52192
Patent Document 7: Japanese unexamined Patent Application Publication No. 2002-60340
Patent Document 8: Japanese unexamined Patent Application Publication No. 11-310602
Patent Document 9: Japanese unexamined Patent Application Publication No. 8-231501
Patent Document 10: Japanese unexamined Patent Application Publication (Translation of PCT Application) No. 2003-514893
Patent Document 11: Japanese unexamined Patent Application Publication (Translation of PCT Application) No. 8-507307

Patent Document 12: WO2005/103089
Patent Document 13: WO2005/097155
Patent Document 14: Japanese unexamined Patent Application Publication No. 2009-132622

SUMMARY OF THE INVENTION

Object to be Solved by the Invention

It has conventionally been considered that the regeneration or repair of a central nervous system damaged due to various factors is difficult. As a result of recent studies, however, it has been revealed that the central nervous system potentially has repair ability. Clinical application of the regenerative ability is highly likely to provide a cure for movement, sensory and memory disorders, and a large number of mental and/or neurological diseases that are considered to be intractable diseases. As a result of the previous studies, the presence of a substance acting to inhibit nerve regeneration and a molecule necessary for regeneration have been discovered, and the effectiveness of target molecular therapy has been suggested in animal studies. On the other hand, in studies regarding the regeneration or repair of the damaged central nervous system, not medical transplantation of ES cells, neural stem cells, etc., but studies directed toward achieving endogenous neural stem cells or activation of endogenous nerve regenerative ability have become the mainstream. With regard to drug discovery having certain targets as well, wide-scale international efforts have begun. An object of the present invention is to provide a non-peptidic nerve axon and/or neurite outgrowth agent for allowing nerve axons and neurites to elongate.

Means to Solve the Object

As a result of intensive studies directed toward solving the aforementioned object, the present inventors have found that 3-(aminocarbonyl)-1-[5-O-[[1-(6-amino-9H-purin-9-yl)-1-deoxy-β-D-ribofuranose-5-O-yl]phosphonyloxy(oxylato) phosphinyl]-β-L-ribofuranosyl]pyridinium (hereinafter also referred to as "NAD analogue of the present invention" at times) has an action to allow nerve axons and neurites to elongate, thereby completing the present invention.

Specifically, the present invention relates to: (1) a compound that is 3-(aminocarbonyl)-1-[5-O-[[1-(6-amino-9H-purin-9-yl)-1-deoxy-β-D-ribofuranose-5-O-yl]phosphonyloxy(oxylato)phosphinyl]-β-L-ribofuranosyl]pyridinium; (2) a nerve axon and/or neurite outgrowth agent (composition), comprising the compound according to (1) above or a pharmacologically acceptable salt thereof as an active ingredient; (3) a cancer cell growth suppressing and/or apoptosis inducing agent (composition), comprising the compound according to (1) above or a pharmacologically acceptable salt thereof as an active ingredient; (4) a method of using the compound according to (1) above or a pharmacologically acceptable salt thereof as a nerve axon and neurite outgrowth agent; (5) a method of using the compound according to (1) above or a pharmacologically acceptable salt thereof as a cancer cell growth suppressing and/or apoptosis inducing agent; (6) a method of using the compound according to (1) above or a pharmacologically acceptable salt thereof for the production of a nerve axon and neurite outgrowth agent; and (7) a method of using the compound according to (1) above or a pharmacologically acceptable salt thereof for the production of a cancer cell growth suppressing and/or apoptosis inducing agent.

In addition, the present invention relates to: (8) a method for producing a compound represented by the following formula (III):

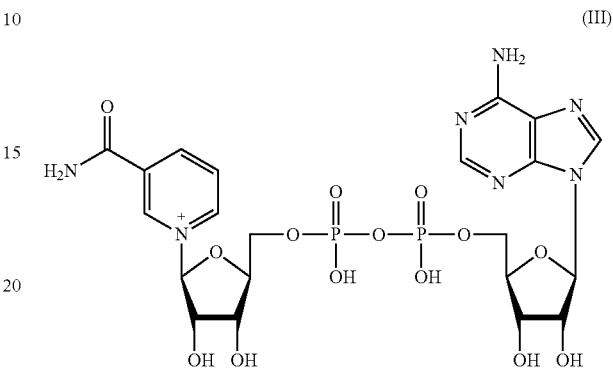

the method comprising reacting a nicotinamide mononucleotide represented by the following formula (I):

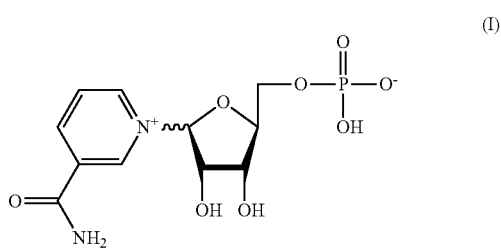

with an adenosine monophosphate morpholidate represented by the following formula (II):

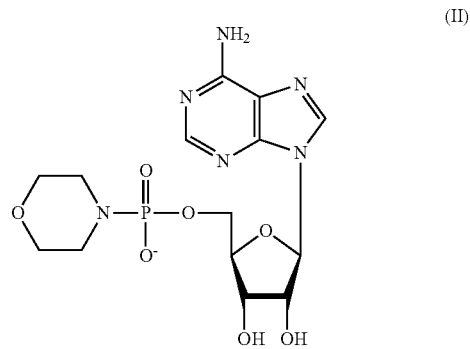

(9) a method for producing a compound represented by the formula (I) recited in (8) above, wherein the nicotinamide mononucleotide represented by the following formula (I):

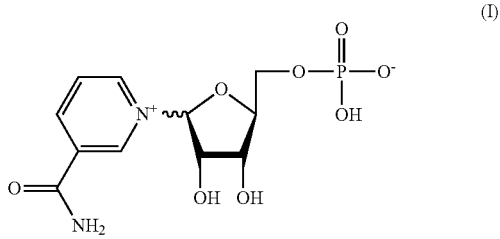

is produced by reacting a nicotinamide represented by the following formula (IV):

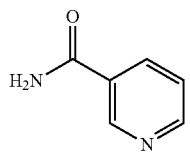

with a L-ribose tetraacetate represented by the following formula (V):

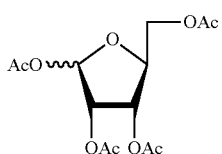

to obtain a nicotinamide mononucleoside represented by the following formula (VI):

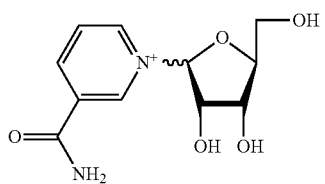

and then phosphorylating the obtained nicotinamide mononucleoside; and (10) a food or a food material comprising the compound according to (1) above or a pharmacologically acceptable salt thereof.

Effect of the Invention

According to the present invention, a nerve axon and/or neurite outgrowth agent capable of allowing a nerve axon and a neurite to elongate and a cancer cell growth suppressing and/or apoptosis inducing agent can be provided.

BRIEF DESCRIPTION OF DRAWINGS

FIG. 5 The figure shows the effect of the NAD analogue of the present invention on Neuro-2a mouse neuroblastoma cells.

FIG. 6 The figure shows the effect of the NAD analogue of the present invention on fetal rat midbrain nerve cells.

FIG. 16 This figure shows the effect of the NAD analogue of the present invention on human neuroblastoma-derived cells (NB-1 cells).

FIG. 17 This figure shows a graph showing the effect of the NAD analogue of the present invention to suppress the growth of human myeloid leukemia cells (HL-60 cells).

FIG. 18A shows a negative control.

MODE OF CARRYING OUT THE INVENTION

Figure 1:
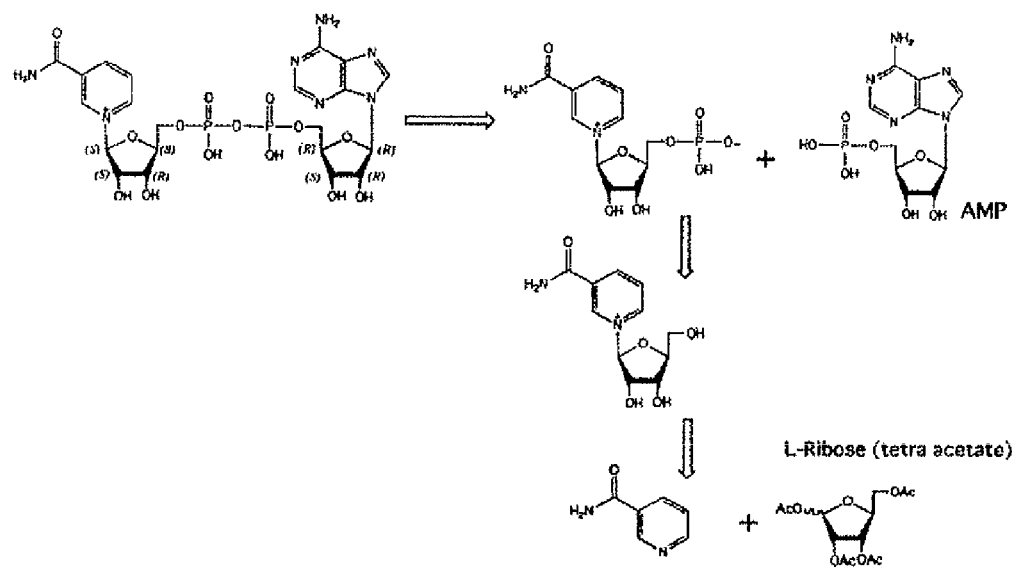
FIG. 1 The figure shows a retrosynthesis scheme for the compound of the present invention.

The compound of the present invention (the NAD analogue of the present invention) can be referred to as 3-(aminocarbonyl)-1-[5-O-[[1-(6-amino-9H-purin-9-yl)-1-deoxy-β-D- ribofuranose-5-O-yl]phosphonyloxy(oxylato)phosphinyl]-β-L-ribofuranosyl]pyridinium. The method for producing the above-described NAD analogue of the present invention is not particularly limited. For example, as shown in the retrosynthesis scheme for the compound of the present invention in FIG. 1, the NAD analogue of the present invention comprising the nicotinamide mononucleotide portion of the present invention containing β-L-ribose as the sugar component can be synthesized by preparing an adenosine monophosphate (AMP) portion and a nicotinamide portion, separately, and then finally preparing a diphosphate form from them. In addition, it has been reported that a nicotinamide portion can be synthesized by condensation reaction between a nicotinamide and an acetyl form of D-ribose. Thus, this method was applied also to L-ribose. That is to say, in the case of producing natural NAD, a nicotinamide mononucleotide containing β-D-ribose as the sugar component is synthesized. In contrast, in the present invention, a nicotinamide mononucleotide containing β-L-ribose as the sugar component (hereinafter also referred to as "the nicotinamide mononucleotide portion of the present invention" at times) is synthesized, and the thus synthesized nicotinamide mononucleotide portion of the present invention and AMP are subjected to a phosphoester bond reaction according to a known synthetic method, thereby obtaining the NAD analogue of the present invention. As AMP, an AMP active complex, a ribose portion of which is natural D-ribose, is preferably used. Moreover, the compound of the present invention may also include the following formula (VII):

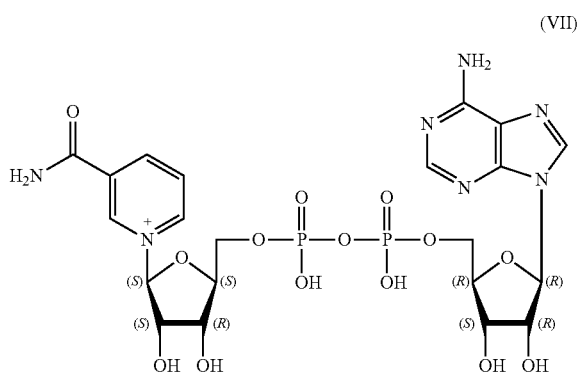

(VII)

Examples of a pharmacologically acceptable salt of the compound of the present invention include pharmacologically acceptable acid-added salts, metal salts, ammonium salts, organic amine-added salts, and amino acid-added salts. Examples of the pharmacologically acceptable acid-added salts include: the inorganic acid salts of hydrochloric acid, hydrobromic acid, sulfuric acid, nitric acid, phosphoric acid and boric acid; the carboxylates as organic acids such as formic acid, acetic acid, propionic acid, fumaric acid, malonic acid, succinic acid, maleic acid, tartaric acid and benzoic acid; sulfonic acids such as methanesulfonic acid and p-toluenesulfonic acid; and amino acid salts of glutamic acid and aspartic acid. Examples of the pharmacologically acceptable metal salts include: alkali metal salts such as lithium, sodium and potassium salts; alkaline earth metal salts such as magnesium and calcium salts; and other metal salts such as aluminum and zinc salts. Examples of the pharmacologically acceptable ammonium salts include the salts of ammonium and tetramethylammonium. Examples of the pharmacologically acceptable organic amine salts include the salts of triethylamine, piperidine, morpholine and toluidine. Examples of the pharmacologically acceptable amino acid-added salts include the added salts of glutamic acid, lysine, glycine and alanine.

The NAD analogue of the present invention can be advantageously used as an agent or a composition for allowing nerve cells such as a nerve axon and/or a neurite to elongate. For instance, the NAD analogue of the present invention is likely to become a novel functional substance used in the treatment of injured central nervous tissues or neurodegenerative diseases. It can be anticipated that the NAD analogue of the present invention can be applied to the functional recovery of nerves, in particular, cranial nerves, damaged by various causes, and to the prevention of age-related functional decline of nerves, in particular, cranial nerves. The usefulness of the NAD analogue of the present invention can be anticipated as an agent for preventing and/or treating diseases that require a nerve cell activating and/or protecting action. Specific examples of such a nerve cell include a midbrain dopaminergic nerve cell, a cerebrocortical nerve cell, a cerebellar cortex nerve cell, and a hippocampal nerve cell. Specific examples of the disease requiring a nerve cell activating and/or protecting action include spinal cord injury, cerebral contusion, brain infarction, cerebral hemorrhage, subarachnoid hemorrhage, Alzheimer's disease, Parkinson's syndrome, multiple sclerosis, demyelinating disease, Guillain-Barre syndrome, and higher brain dysfunction. Among these diseases, a preferred example is Parkinson's syndrome.

The NAD analogue of the present invention can also be used as a cancer cell growth suppressing and/or apoptosis inducing agent. Examples of cancer, for which the cancer cell growth suppressing and/or apoptosis inducing agent of the present invention is effective, include: cancers or tumors in which epithelial cells and the like become malignant, such as malignant melanoma (melanoma), skin cancer, lung cancer, tracheal and bronchial cancer, oral epithelial cancer, esophageal cancer, stomach cancer, colon cancer, rectal cancer, bowel cancer, liver and intrahepatic bile duct cancer, kidney cancer, pancreatic cancer, prostatic cancer, breast cancer, uterine cancer, ovary cancer and cerebral tumor; cancers or tumors in which muscles or bones that are cells constituting supporting tissues become malignant, such as myosarcoma, osteosarcoma and Ewing's sarcoma; and hematopoietic cell-derived cancers or tumors such as leukemia, malignant lymphoma, myeloma and Burkitt's lymphoma. Among these cancers and tumors, most reliable examples include: the aforementioned cancers or tumors in which epithelial cells become malignant; and leukemia, because the NAD analogue of the present invention suppresses the growth of human myeloid leukemia cells and also induces apoptosis of the human myeloid leukemia cells, and has the effect of suppressing the growth of leukemia cells that are resistant to retinoic acid.

When the NAD analogue of the present invention is used as an agent or a composition for allowing nerve axons and/or neurites to elongate, or as a cancer cell growth suppressing and/or apoptosis inducing agent, and particularly when it is used as a pharmaceutical preparation, various types of mixing ingredients for preparations, such as a pharmaceutically acceptable common carrier, binder, stabilizer, excipient, diluent, pH buffering agent, disintegrator, solubilizer, solubilizing aid or isotonizing agent, can be added to the above-mentioned ingredients.

The type of a food or food material used for the functional recovery of nerves, particularly the functional recovery of cranial nerves, or for the prevention and/or treatment of cancer, which comprises the NAD analogue of the present invention or a pharmacologically acceptable salt thereof, is not particularly limited. The term "functional recovery of nerves" is used herein to mean that the aforementioned food or food material is able to exhibit a nerve cell activating and/or protecting action. In addition, the term "prevention and/or treatment of cancer" is used herein to mean that the aforementioned food product or food material is able to exhibit the effect of preventing cancer or improving cancerous symptoms. Specific examples of the food (products) or food material(s) include: various types of beverages such as yogurt, drink yogurt, juice, milk, soymilk, alcoholic beverages, coffee, black tea, green tea, Oolong tea and sports drink; breads and/or confectionaries including baked goods such as pudding, cookies, bread, cake, jelly and Japanese rice cracker, Japanese sweets such as yokan (sweet bean jelly), frozen desserts, and chewing gum; noodles such as udon and soba noodles; fish paste products such as kamaboko, ham and fish meat sausage; condiments such as miso, soy sauce, dressing, mayonnaise and sweetener; dairy products such as cheese and butter; tofu; konjac food; and various types of prepared food products such as food boiled in soy sauce, dumplings, croquettes or salad. Known nerve axon and/or neurite outgrowth agents or known substances having an action to suppress the growth of cancer cells and/or to induce apoptosis of the cancer cells may be used in combination with these food products or food materials.

EXAMPLES

Hereinafter, the present invention will be more specifically described in the following Examples. However, these examples are not intended to limit the technical scope of the present invention.

Example 1

Synthesis of the NAD Analogue of the Present Invention

The NAD analogue of the present invention, which contained, as a constituent sugar of a nicotinamide mononucleotide thereof, β-L-ribose that is an enantiomer of the β-D-ribose portion of the nicotinamide portion of NAD, was chemically synthesized. Then, the effect of the NAD analogue to allow neurites to elongate was examined. The NAD analogue of the present invention was synthesized in accordance with the following steps.
[Synthesis of Nicotinamide Mononucleotide Portion of the NAD Analogue of the Present Invention]

Figure 2:
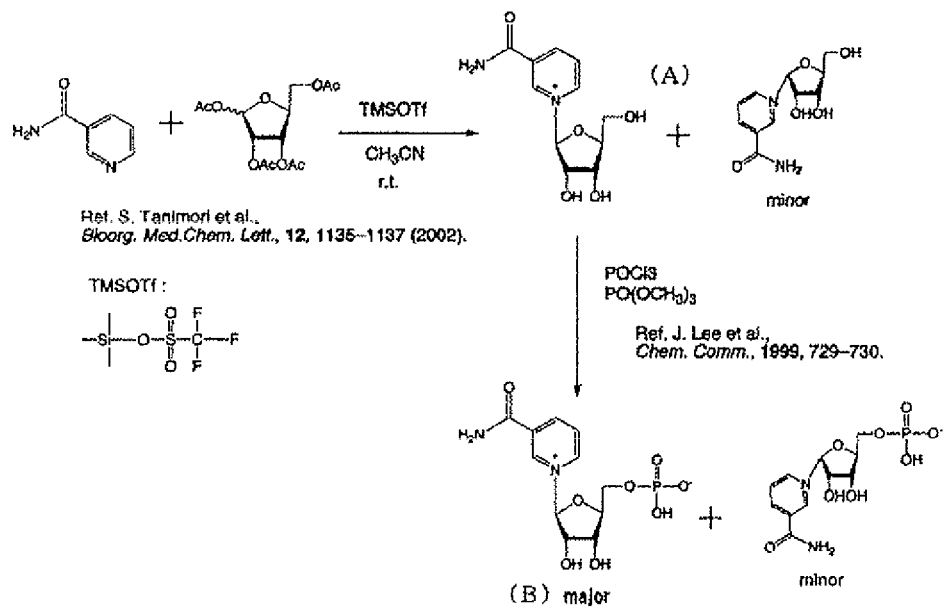
FIG. 2 The figure shows a step of synthesizing the nicotinamide mononucleotide portion of the present invention comprising β-L-ribose as the sugar component.

In accordance with the method of Tanimori et al. for synthesizing nicotinamide riboside from nicotinamide and ribose (see Bioorg. Med. Chem. Lett., 12, 1135-1137 (2002)) and the method of J. Lee et al. comprising a phosphorylation reaction of the 5-hydroxyl group of a ribose portion (Chem. Comm., 1999, 729-730), the nicotinamide mononucleotide portion of the present invention was synthesized as a nicotinamide mononucleotide containing β-L-ribose as the sugar component (see FIG. 2). Specifically, 172 mg of nicotinamide (manufactured by Wako Pure Chemical Industries, Ltd.) and 400 mg of L-ribose tetraacetate (manufactured by Sigma) were dissolved in 10 mL of anhydrous acetonitrile, and an excessive amount of trimethylsilyl trifluorosulfonate (TM-SOTf) was added to the resulting solution under a nitrogen flow. Thereafter, the reaction solution was stirred at a room temperature for 1 hour 30 minutes. Thereafter, 5.0 mL of methanol was added to the reaction solution to terminate the reaction. The obtained reaction solution was subjected to a column (diameter: 1.5 cm×length: 3 cm) filled with activated carbon (manufactured by Wako Pure Chemical Industries, Ltd.), and it was washed with distilled water and was then eluted with methanol, so as to recover a product.

As a result of NMR analysis, the ratio of glycoside bonds was assumed to be α:β=about 7:1, and the above product was a mixture of anomeric isomers with a L-ribose portion at position 1 (see FIG. 2(A)). If left at a room temperature, the product would decompose. Thus, without performing a further purification, the hydroxyl group at position 5 of the L-ribose portion was subjected to a phosphorylation reaction.

258 mg of the above product was dissolved in 1.5 mL of trimethoxyphosphoric acid, and thereafter, 0.25 mL of phosphorus oxychloride was added dropwise to the resulting solution under cooling on ice. The reaction solution was stirred under a nitrogen flow at 0° C. for 20 hours. Thereafter, a 2 N sodium hydroxide aqueous solution was added to the reaction solution for neutralization, so as to terminate the reaction. To the obtained reaction solution, 2.0 mL of cold acetonitrile-ether (1:3) solution was added, so as to perform phase-separation. The lower layer (water phase) was subjected to an anion exchange resin (Amberlite IRA410; formic acid form; manufactured by Rohm and Haas Company) (diameter: 1.7 cm×length: 8.5 cm) to recover a reaction product. Thereafter, the reaction product was subjected to a cation exchange resin (Amberlite IR120B; $H^+$ form; manufactured by Rohm and Haas Company) (diameter: 1.0 cm×length: 12 cm) for further purification, so that 238 mg of a fraction that was assumed to be the nicotinamide mononucleotide portion of the present invention was recovered in the form of a freeze-dried product.

The chemical structure of a compound contained in the above fraction was confirmed by MS, $^1$H-NMR, $^{13}$C-NMR and $^{31}$P-NMR. After the above-described two steps, the yield of the nicotinamide mononucleotide portion of the present invention was approximately 70%, which was almost the same as that described in the aforementioned document, Tanimori et al. (see FIG. 2(B)).
[Phosphoester Bond of AMP and the Nicotinamide Mononucleotide Portion of the Present Invention]

Figure 3:
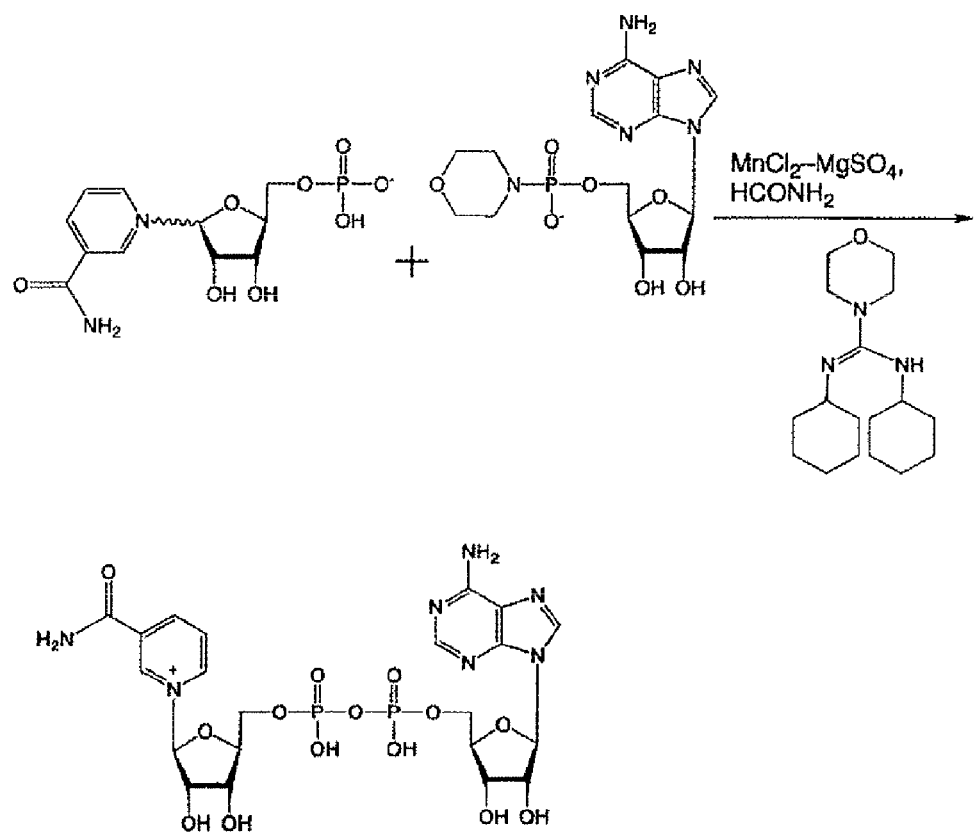
FIG. 3 The figure shows a step of synthesizing a phosphoester bond of AMP and the nicotinamide mononucleotide portion of the present invention.

FIG. 3 shows a step of forming a phosphoester bond between AMP and the nicotinamide mononucleotide portion of the present invention. As AMP, a commercially available AMP active complex (AMP-morpholidate) containing VD-ribose as a ribose portion was used.

The above obtained nicotinamide mononucleotide portion of the present invention was dissolved in a formamide solution of 0.2 M manganese chloride (1.5 equivalences), and thereafter, AMP-morpholidate (1 equivalence) (manufactured by Sigma) and magnesium sulfate (2 equivalences) were added to the resulting solution. The reaction solution was stirred under a nitrogen flow at a room temperature for 21 hours. After the reaction, cold acetonitrile was added to the reaction solution, so that the solution became clouded. Then, the reaction solution was centrifuged, so that a supernatant was discarded and a precipitate was recovered. The precipitate was subjected to Sephadex LH-20 column chromatography (manufactured by Pharmacia), and it was then eluted with distilled water, so as to prepare a fraction containing a main product. Since this fraction was found to have weak neurite outgrowth activity, it was suggested that the fraction should contain the NAD analogue of the present invention although its reaction yield was not high.
[Purification of the NAD Analogue of the Present Invention]

The NAD analogue of the present invention was purified using a HPLC-PDA system consisting of a L-2130 pump, a L-2450 photodiode array detector (PDA), a L-2200 autosampler and a L-2300 column oven (all of which are manufactured by Hitachi High-Technologies Corporation) and a fraction collector SF-2100 (manufactured by Advantec Toyo Kaisha, Ltd.). HPLC separation conditions are as follows.
Column: Cosmosil Packed Column HILIC, 250 mm×4.6 mm i. d. (manufactured by Nacalai Tesque, Inc.)
Sample concentration: 40 mg/mL ($H_2O$)
Amount injected: 30 μL
Column temperature: 40° C.
Flow rate: 1 mL/min
Solvent A: $H_2O$
Solvent B: 100 mmol $CH_3COONH_4$ aqueous solution
Gradient: A:B=90:10 (0 minute), 70:30 (13 minutes), 0:100 (15 minutes), 0:100 (18 minutes), 90:10 (19 minutes), 90:10 (25 minutes)
Separatory conditions: 0 to 25 minutes, 25 fractions (separatory interval: 1 minute)

Figure 4:
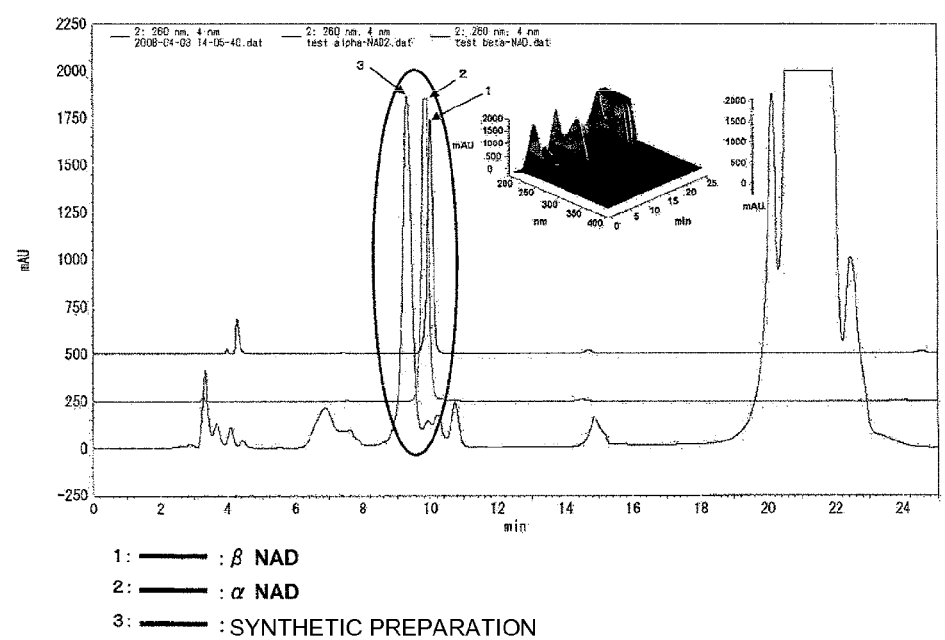
FIG. 4 The figure shows a compound purification chart showing purification of the NAD analogue of the present invention by HPLC.

A purification chart of a compound purified under the above-described HPLC conditions is shown in FIG. 4. As standard substances, commercially available α-NAD (whose nicotinamide mononucleotide portion contains α-D-ribose as the sugar component) (manufactured by Sigma) and β-NAD (whose nicotinamide mononucleotide portion contains β-D-ribose as the sugar component) (manufactured by Sigma) were used. Peaks of the α-NAD and β-NAD were observed around 9.8 minutes. Differing from these two peaks, a peak of a compound purified in the present example was observed around 9.3 minutes. Thus, it was confirmed that the compound purified under the aforementioned HPLC conditions was the NAD analogue of the present invention, which was different from the α-NAD and β-NAD.

Hereinafter, the NAD analogue of the present invention was identified by the following method.

Mass (FAB MS) spectrometry was carried out using JMS-700T manufactured by JEOL Ltd. (ion source: Xe atom beam; accelerating voltage: 10 Kv; resolution power: 5000). A proton nuclear magnetic resonance spectrum ($^1$H-NMR: 500 MHz) and a carbon nuclear magnetic resonance spectrum ($^{13}$C-NMR: 125 MHz) were measured using JNM-A500 manufactured by JEOL Ltd. (sample concentration: 1.5% (w/v %), measurement concentration: 35° C.; solvent: $D_2O$; and digital resolution power: $^1$H-NMR (500 MHz) 0.31 Hz and $^{13}$C-NMR (125 MHz) 1.03 Hz). The chemical sifts were indicated in δ values (ppm), using tetramethylsilane (TMS) as an internal standard, and the coupling constant (J) was expressed in Hz. Signals were expressed with the following abbreviations: "s: singlet, d: doublet, t: triplet, q: quartet, dd: double doublet, td: triplet doublet, and m: multiplet" (see Table 1, etc.).

Figure 9:
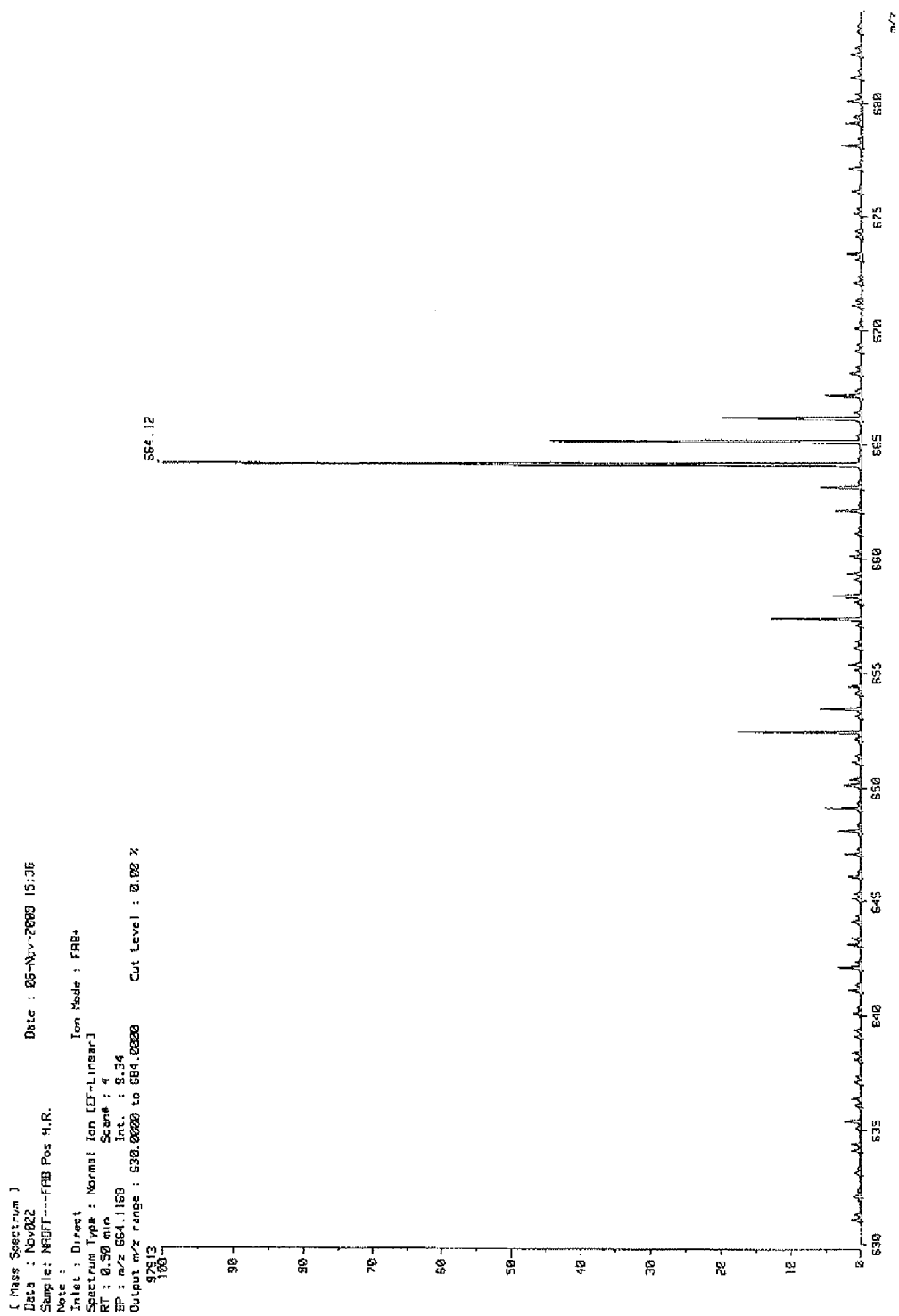
FIG. 9 The figure shows the analysis results obtained by performing MS (mass spectrometry) on the NAD analogue of the present invention.
Figure 10:
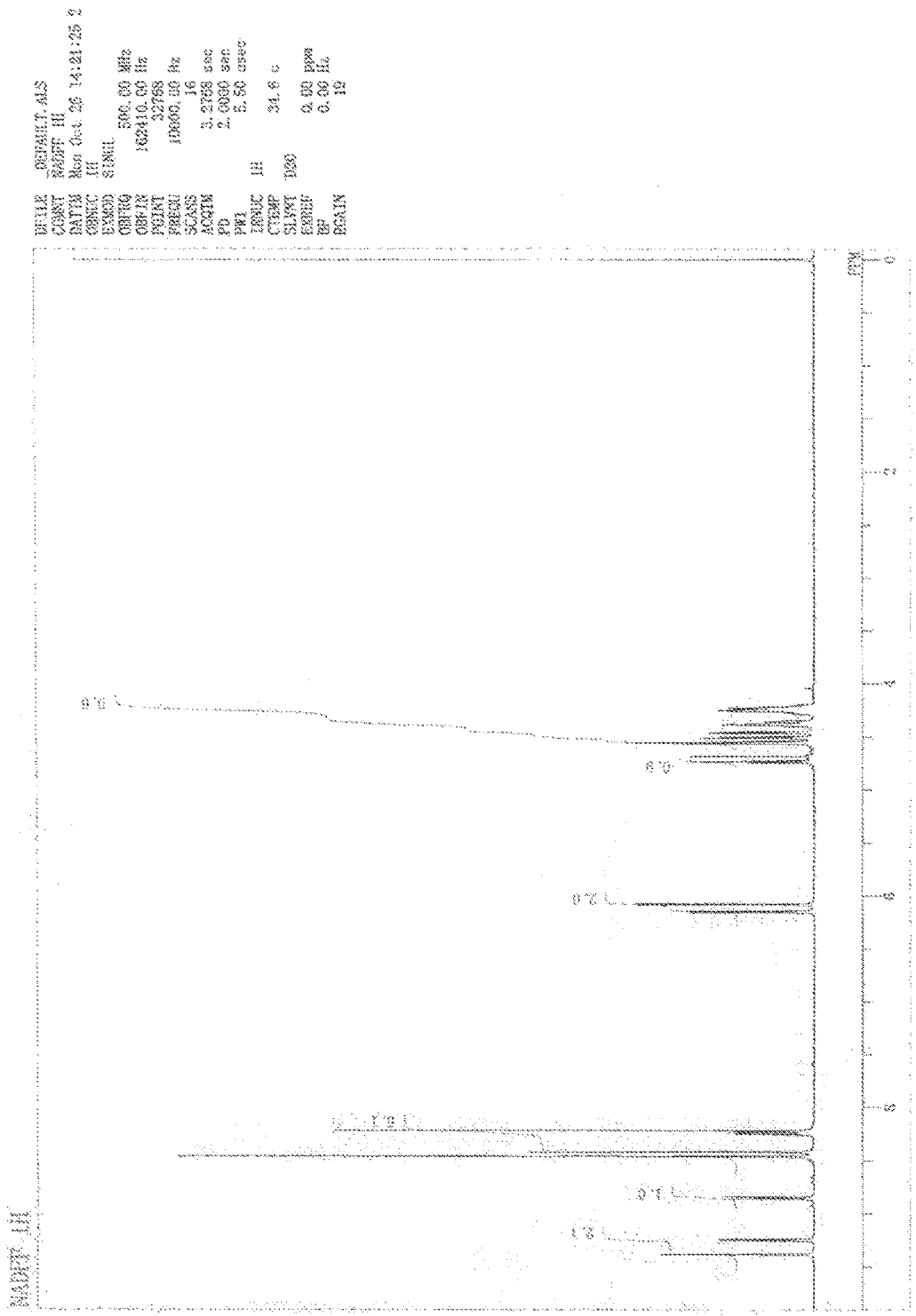
FIG. 10 The figure shows the results of the proton nuclear magnetic resonance spectrum ($^1$H-NMR) of the NAD analogue of the present invention.
Figure 11:
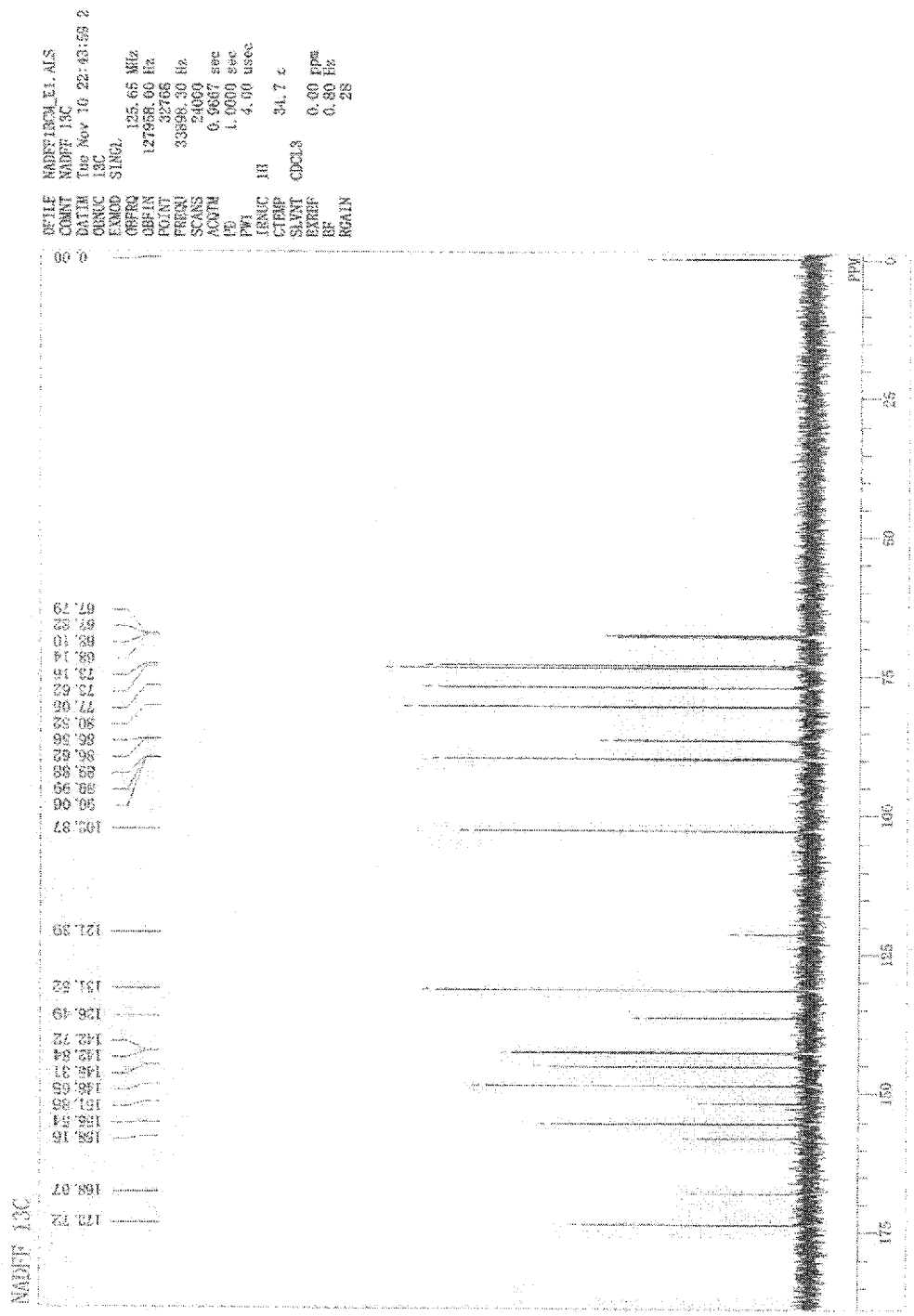
FIG. 11 The figure shows the results of the carbon nuclear magnetic resonance spectrum ($^{13}$C-NMR) of the NAD analogue of the present invention.
Figure 12:
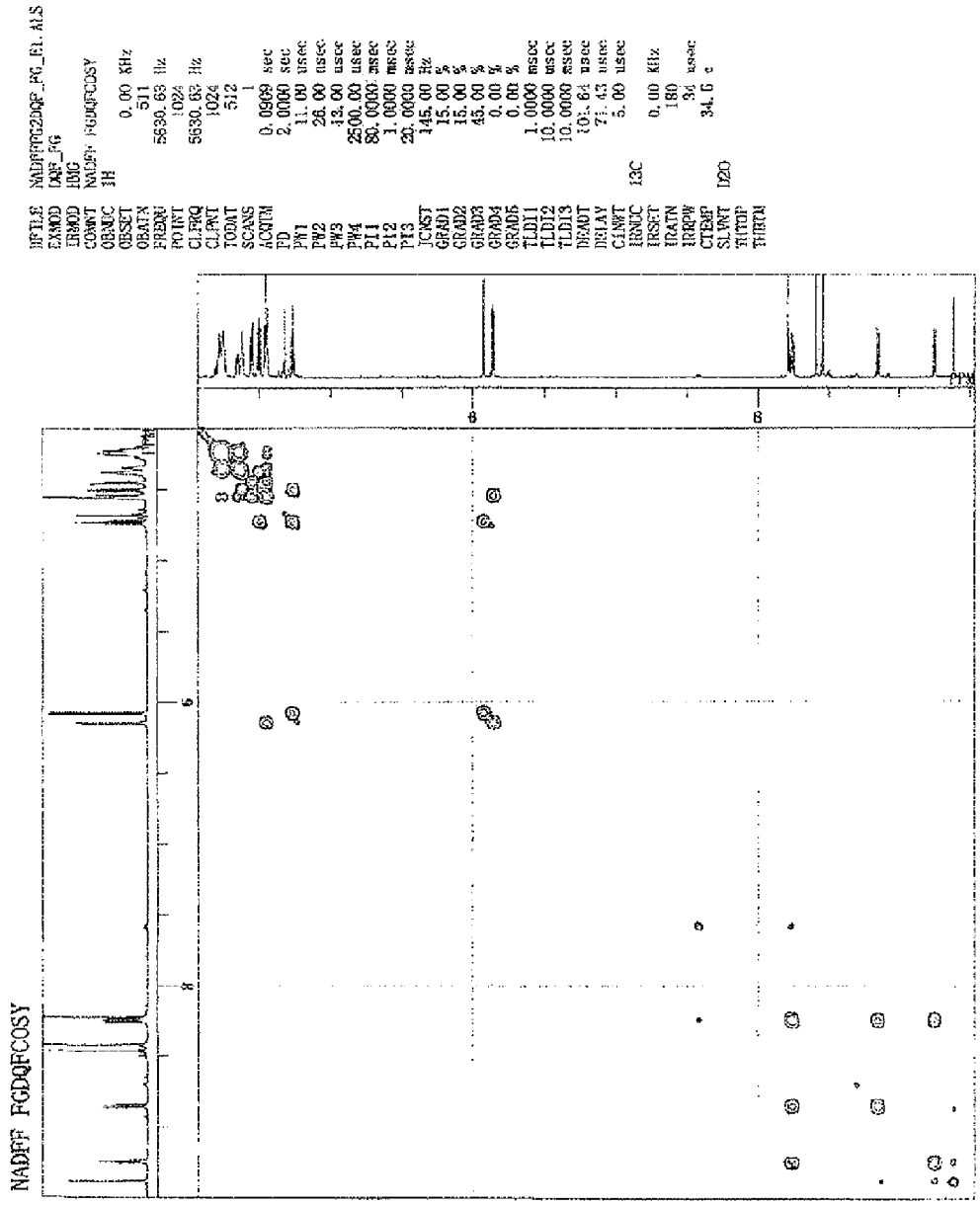
FIG. 12 The figure shows the results of the two dimensional H-HCOSY of the NAD analogue of the present invention.
Figure 13:
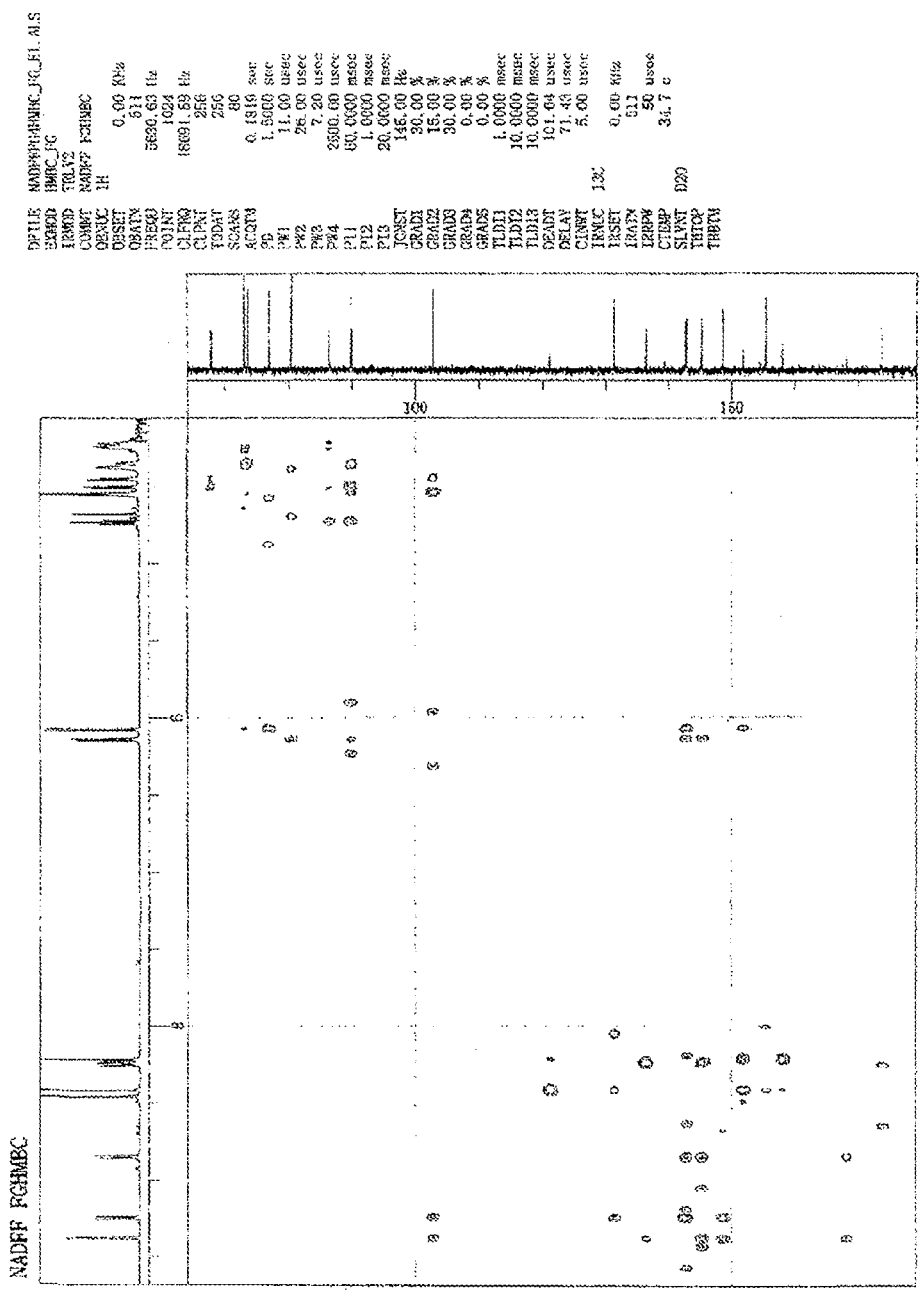
FIG. 13 The figure shows the results of the two dimensional HMBC of the NAD analogue of the present invention.
Figure 14:
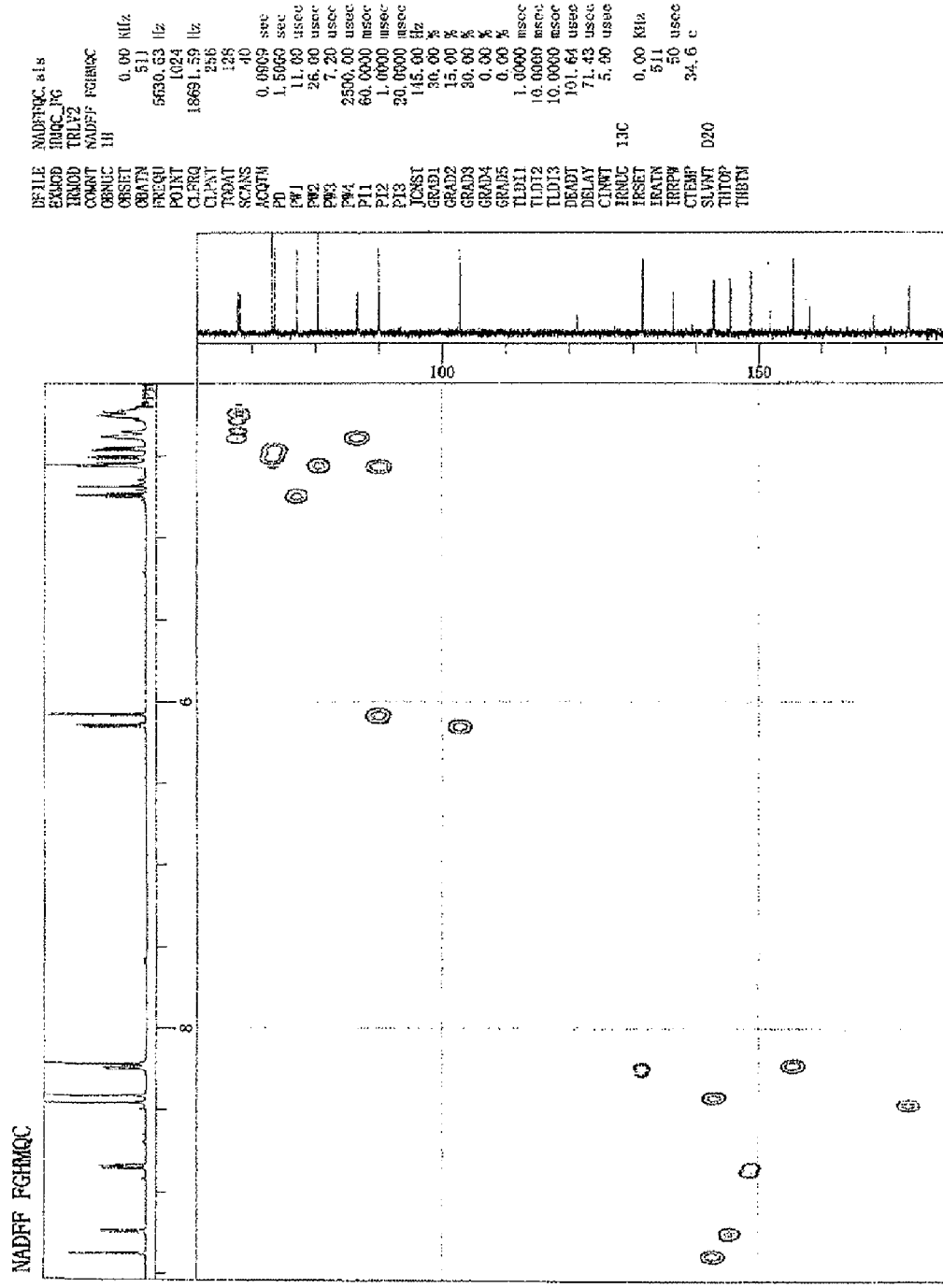
FIG. 14 The figure shows the results of the two dimensional HMQC of the NAD analogue of the present invention.

The results of the mass spectrometry (MS) are shown in FIG. 9, the results of the proton nuclear magnetic resonance spectrum ($^1$H-NMR) are shown in FIG. 10, the results of the carbon nuclear magnetic resonance spectrum ($^{13}$C-NMR) are shown in FIG. 11, the results of two dimensional H-HCOSY are shown in FIG. 12, the results of two dimensional HMBC are shown in FIG. 13, and the results of two dimensional HMQC are shown in FIG. 14. In addition, attributions of $^1$H-NMR and $^{13}$C-NMR are shown in the following Table 1 and formula (VIII).

TABLE 1

|  | $^1$H | $^{13}$C |
|---|---|---|
| N-2 | 9.39(1H, S) | 142.8 |
| N-3 |  | 136.5 |
| N-4 | 8.85(1H, td, J = 1.5, 7.9) | 148.7 |

TABLE 1-continued

|  | $^1$H | $^{13}$C |
|---|---|---|
| N-5 | 8.24(1H, dd J = 6.4, 7.9) | 131.5 |
| N-6 | 9.24(1H, d, J = 6.4) | 145.3 |
| $CONH_2$ |  | 168.1 |
| N-1' | 6.15(1H, d, J = 5.8) | 102.9 |
| N-2' | 4.56(1H, t, J = 5.5) | 80.2 |
| N-3' | 4.45(1H, q, J = 2.5) | 73.6 |
| N-4' | 4.35(1H, dd, J = 2.4, 4.2) | 90.06, 89.99 |
| N-5' | 4.22-4.26(m) | 67.82, 67.74 |
| A-2 | 8.41(1H, s) | 142.7 |
| A-4 |  | 121.4 |
| A-5 |  | 151.9 |
| A-6 |  | 158.2 |
| A-8 | 8.22(1H, s) | 155.5 |
| A-1' | 6.08(1H, d, J = 5.8) | 89.9 |
| A-2' | 4.74(1H, t, J = 5.1) | 77.1 |
| A-3' | 4.50(1H, dd, J = 5.2, 4.0) | 73.2 |
| A-4' | 4.38(1H, m) | 86.62, 86.56 |
| A-5' | 4.22-4.26(m) | 68.14, 68.30 |

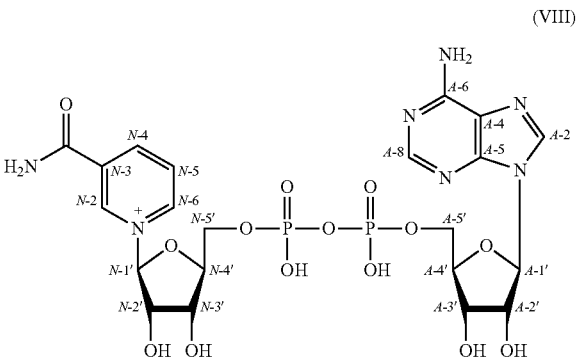

(VIII)

(Results)

As a result of performing high-resolution MS measurement, the accurate mass of a protonated molecule ((M+H)$^+$) of m/z=664 was found to be 664.1168. Constituent elements were defined as C, H, N, S and P, and a composition operation was then carried out. $C_{21}H_{28}N_7O_{14}P_2$ was selected as a composition formula. From the results of the MS and the nuclear magnetic resonance spectra, the obtained NAD analogue of the present invention was determined to be a novel compound having a structure represented by the above-described formula (VII). The above formula (VII) can also be referred to as 3-(aminocarbonyl)-1-[5-O-[[1-(6-amino-9H-purin-9-yl)-1-deoxy-β-D-ribofuranos-5-O-yl]phosphonyloxy(oxylato) phosphinyl]-β-L-ribofuranosyl]pyridinium, which is a systematic name.

Example 2

Effect of the NAD Analogue of the Present Invention on Morphology of Nerve Cell (1)

[Effect of the NAD Analogue of the Present Invention on Mouse Neuroblastoma Cells]

Using mouse-derived neuroblastoma cells that are model cells used to examine neurite outgrowth effect, the inductive action of the NAD analogue of the present invention on the outgrowth of neurites was examined. Mouse-derived neuroblastoma cells (Neuro-2a cells) (obtained from the Health Science Research Resources Bank) were adjusted to a concentration of 10$^6$ cells/mL, and the cells were then cultured at 37° C. in a 10% fetal bovine serum-added Eagle's minimal essential (EME) medium culture solution in the presence of 5% $CO_2$.

The above-described Neuro-2a cells were cultured for 3 hours, and the medium was then exchanged with a fresh one of the same type as described above. Then, 10 μg/mL of the NAD analogue of the present invention was added thereto, and the culture was further continued for 48 hours. Thereafter, the morphological alteration of the cell was observed under a phase-contrast microscope. The results are shown in FIG. 5. It is clear that neurites (nerve axon-like projections) appeared from Neuro-2a cells and that these neurites elongated from the cells ((a), arrows). In a case in which a control (b), which did not contain the NAD analogue of the present invention, was cultured, such a nerve axon-like projection structure was slightly observed. However, when compared with the case of adding the NAD analogue of the present invention to the cells, the length of such a neurite was apparently short. Moreover, the same experiment as described above was carried out using commercially available β-NAD. As a result, no change in neurites was found.

[Effect of the NAD Analogue of the Present Invention on Fetal Rat Midbrain Dopaminergic Nerve Cells]

Fetuses were removed from a Sprague-Dawley (SD) rat that was 15 days pregnant, and a ventral portion of midbrain was then cut out under a stereoscopic microscope. The obtained portion was chopped with a surgical knife, and was then treated at 37° C. in a 0.25% trypsin-containing PBS for 20 minutes, so that the cells were dispersed. Thereafter, the resulting cells were treated with PBS that contained 50 μg/mL deoxyribonuclease (DNase I) and 50 μg/mL trypsin inhibitor at 37° C. for 5 minutes, so as to obtain fetal rat midbrain dopaminergic nerve cells. The thus obtained fetal rat midbrain dopaminergic nerve cells were cultured at 37° C. in a 10% bovine serum-added Dulbecco's modified Eagle's medium (DMEM) culture solution in the presence of 5% $CO_2$.

The above-described fetal rat midbrain dopaminergic nerve cells were cultured for 2 days, and the culture solution was then exchanged with a fresh one. The NAD analogue of the present invention was added to the cells in various concentrations of 0 (control), 0.01, 0.1, 1.0 and 10 μg/mL, and the obtained mixture was further cultured for 3 days. On the 5th day of the culture, the dopaminergic nerve cells were stained with an anti-tyrosine hydroxylase antibody (manufactured by Pel-Freez) and a Fluorescein (FITC)-labeled secondary antibody (manufactured by Jackson ImmunoResearch Laboratories, Inc.) according to an immunostaining method. Then, the length and number of neurites elongated from the cell bodies of the stained cells were then measured using Neurolucida (manufactured by Micro Bright Field). The results are shown in FIG. 6. From the data obtained in the concentration range of 0 to 10 μg/mL, it was found that, the higher the concentration of the NAD analogue of the present invention in the fetal rat midbrain nerve cells, the longer a neurite was clearly, in comparison to the control. Thus, it became clear that the NAD analogue of the present invention provides the outgrowth of a nerve axon, and at the same time, it forms a large number of knobby, what is called "varicosities" on the projection, and that the NAD analogue of the present invention thereby enables synapse formation that would lead to nerve regeneration. Moreover, the same experiment as described above was carried out using commercially available β-NAD. As a result, the outgrowth of neurites was not observed.

Figure 7:
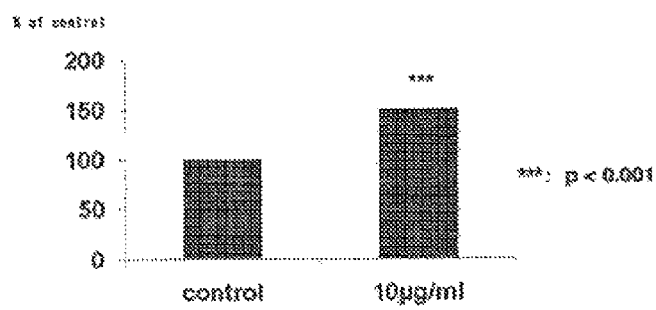
FIG. 7 The figure shows the effect of the NAD analogue of the present invention to allow neurites to elongate from fetal rat brain dopaminergic cells.

FIG. 7 shows the results obtained by examining the effect of the NAD analogue of the present invention to allow neurites to elongate from fetal rat brain dopaminergic cells. The lengths of neurites elongated from the cells were measured, and a comparison was made on the measurement results. When 10 μg/mL of the NAD analogue of the present invention was added to the cells, the length of the obtained neurite became approximately 150% if the length of a neurite in the control was defined as 100%. Thus, it was found that the NAD analogue of the present invention apparently exhibited a neurite outgrowth effect. It is noted that 45 control cells and 38 test cells were subjected to the measurement, and the results were shown as average values.

Figure 8:
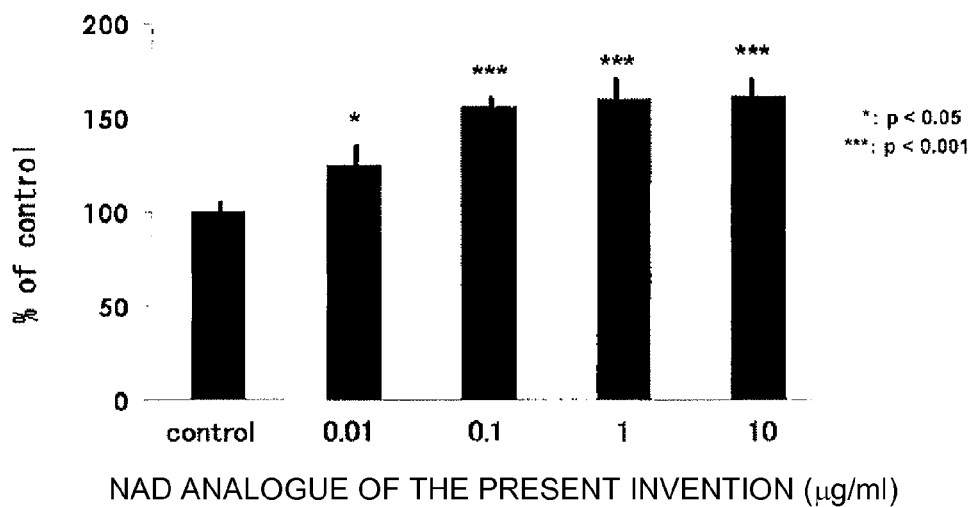
FIG. 8 The figure shows a difference in the effect of the NAD analogue of the present invention to allow neurites to elongate from fetal rat brain dopaminergic cells, depending on concentration of the NAD analogue.

FIG. 8 is a graph showing a quantitative change in the effect of the NAD analogue of the present invention to allow neurites to elongate from fetal rat brain dopaminergic cells. It was found that addition of 0.1 μg/mL of the NAD analogue of the present invention allows neurites to elongate from the fetal rat brain dopaminergic cells. Moreover, the same experiment as described above was carried out using commercially available β-NAD. As a result, the outgrowth of neurites was not observed.

Example 3

Effect of the NAD Analogue of the Present Invention on Shape of Nerve Cell (2)

[Effect of the NAD Analogue of the Present Invention on Human Neuroblastoma Cell-Derived NB-1 Cells]

Using human neuroblastoma cell-derived cells as model cells for neurite outgrowth, the action of the NAD analogue of the present invention to induce the outgrowth of neurites was examined. Human-derived neuroblastoma cells (NB-1 cells) (obtained from the Health Science Research Resources Bank) were adjusted to a concentration of $10^3$ cells/mL, and the cells were then cultured at 37° C. in a 10% fetal bovine serum-added Eagle's minimal essential medium (EME) culture solution in the presence of 5% $CO_2$.

Figure 15:
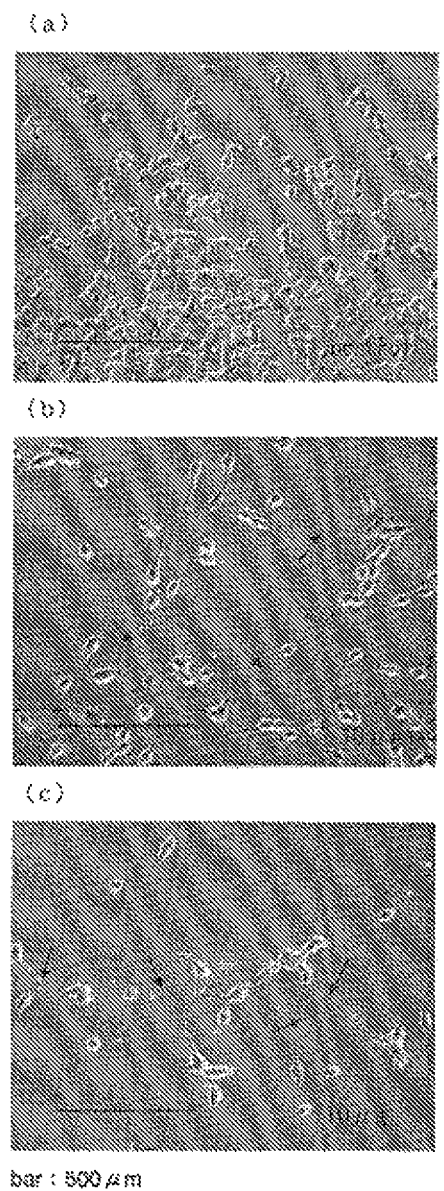
FIG. 15 The figure shows the effect of the NAD analogue of the present invention on human neuroblastoma cell-derived NB-1 cells. In the figure, (a) shows a control, and (b) and (c) show the case of adding the NAD analogue in a concentration of 10 μg/mL. The arrow indicates a neurite.

The above-described NB-1 cells were cultured for 3 hours, and the medium was then exchanged with a fresh one of the same type as described above. Then, 10 μg/mL of the NAD analogue of the present invention was added thereto, and the culture was further continued. Thereafter, the morphological alteration of the cells was observed under a phase-contrast microscope. During the culture, the culture solution was exchanged with a fresh one every 4 or 5 days. The cells were observed on the 10th day after initiation of the culture and the results are shown in FIG. 15. It is clear that neurites (nerve axon-like projections) appeared from NB-1 cells and that these neurites elongated from the cells (see FIGS. 15(b) and 15(c)). In a case in which a control (see FIG. 15(a)), which did not contain the NAD analogue of the present invention, was cultured, such a nerve axon-like projection structure was slightly observed. However, when compared with the case of adding the NAD analogue of the present invention to the cells, the length of such a neurite was apparently short. Moreover, the same experiment as described above was carried out using commercially available β-NAD. As a result, no change in neurites was found.

Example 4

Analysis of Gene Expression Using Microarray

The NAD analogue of the present invention was added to rat nerve cells during the culture of the cells, and gene expression in the nerve cells was then examined by microarray analysis.

[Test Method]

As nerve cells, fetal rat linear nerve cells (dopaminergic cells) purchased from LONZA (U.S.A.) were used. The cells were adjusted to a concentration of $1.0 \times 10^5$ cells/mL, and were then cultured at 37° C. in the presence of 5% $CO_2$. As a culture solution, a serum-free medium for primary nerve cell culture (manufactured by LONZA) was used, and it was prepared according to the protocols. A culture dish, the surface of which had been treated with polylysine, was used. The NAD analogue of the present invention was adjusted to a final concentration of 10 μg/mL in the culture solution. The NAD analogue of the present invention was added simultaneously at the start of cell culture. 24 hours later, RNA was extracted from the cells using TRIZOL (registered trademark) (Invitrogen) according to an ordinary method, and the extracted RNA was used as a sample on Day 1. Thereafter, 48 hours after initiation of the cell cultur, RNA was extracted from the cells, and it was used as a sample on Day 2. It is to be noted that a culture, to which the NAD analogue of the present invention had not been added, was used as a negative control.

With regard to the RNA sample on Day 1 and the RNA sample on Day 2, each of which was extracted from the fetal rat linear nerve cells after the culture, gene expression in the nerve cells was analyzed by Cell Innovator Inc. (Fukuoka, Japan) on a commission basis.

The RNA samples on Day 1 and Day 2 extracted from the fetal rat linear nerve cells were subjected to a microarray test using Rat Genome 230 2.0 Array manufactured by Affymetrix, Inc. (U.S.A.). Overall, it was found that the alteration of gene expression caused by addition of the NAD analogue of the present invention is small. This result is highly likely to show that the NAD analogue of the present invention has low toxicity as an agent.

Giving attention to the sample on Day 2 whose altered expression was larger than that of the sample on Day 1, genes whose expression was altered were extracted, and were then analyzed by IPA (Ingenuity Pathways Analysis). The results obtained by analyzing the sample on Day 2 by IPA are shown in the following Table 2. It was confirmed that genes regarding cytoskeleton or nerve cells underwent altered expression.

TABLE 2

| /ID | Molecules in Network | Score | Focus Molecules | Top Functions |
|---|---|---|---|---|
| 1 | Alpha tubulin, ↓ATRX, ↑BNC2, ↓C16ORF53, ↓C20ORF191, ↓CAMK2G, ↑CDX1, Ctbp, Cyclin A, Cyclin D, Cyclin E, E2f, Estrogen Receptor, ↑GFER, ↑GOLT1B, Hdac, ↓HDAC5, ↓LUC7L2, ↑MECOM, N-cor, ↓NASP, ↓NCOA6, NFkB (complex), Nuclear factor 1, ↓PTN, Rb, ↓RB1, ↓RBM39, ↓RIOK3, Rxr, ↓S100B, ↓SF3B1, ↓SF3B2, ↑STK38, ↑WTAP | 36 | 22 | Cell Cycle, Cell Death, *Nervous System Development and Function* |
| 2 | ↓ACTR6, ↓AK2, Ap1, APC, ↓AQP4, ↓ASH1L, ↑ASNS, ATPase, ↓BRD8, ↓CEBPD, Ck2, ↑CREBBP, ↓DDIT3, Fibrinogen, ↑HBB (includes EG:3043), HISTONE, Histone h3, IgG, IL1, IL12 (complex), LDL, ↑LYZ, ↓MLL, P38 MAPK, ↓PDCD4*, ↓PLS3, ↓PSMC6*, ↓RANBP2, RNA polymerase II, ↑RUVBL1, ↓SLBP, ↓SMARCA5, ↓TNFSF13, ↓TOP2B, ↑TRIM16 | 35 | 22 | *Skeletal and Muscular System Development and Function*, Cell Morphology, Cellular Compromise |
| 3 | ALDH3A1, ↓ARL6, ↓ARMC8, ↑ASNS, ↓BAI1, ↓CFL2, CYP4F2, ↑DDX10, ↓EIF5, ERO1L, ↑FH, ↓FN3KRP, GPX2, HNF4A, ↓HOOK3, ↑IGFBF7, ↓LAP3, MKRN1, ↓MTMR4, NAA10, ↓NFX1, ↑NSA2, PEG10, ↓PURG, RABEPK, retinoic acid, ↓RPRD1B, RPS20, SEC61B, SLC35A2, SSR3, ↓TBC1D15, TERT, ↑TM7SF2, ↑UBASH3B | 32 | 20 | Cell Cycle, Gene Expression, Lipid Metabolism |
| 4 | ↑ACVR1, Alp, BCR, BMP, ↑BMP6, CD3, ↓CIRBP, ↓CYTH3, ERK1/2, ↑FRMD4B, Growth hormone, GST, ↑GSTM1, ↑GSTM5, Integrin, Laminin, ↑LGALS1, Lpa receptor, MAP2K1/2, Mek, ↓NFE2L2, ↓NOG, ↑PDLTM7, PI3K p85, ↓PIK3CA, ↓PTK2, ↓RAB1A, ↑RAB33B, Rap1, ↓RAP1A, Smad1/5/8, ↑SORL1, Sos, ↑SPP1, TCR | 28 | 18 | Cellular Development, *Skeletal and Muscular System Development and Function*, Cardiovascular System Development and Function |
| 5 | alcohol group acceptor phosphotransferase, AMPK, ↓ARFGAP1, ↓ARHGEF12, Calcineurin A, Calmodulin, Calpain, CAMKII, Creb, ↑CSNK1D, Cytochrome c oddase, ↓GABPA, Gsk3, ↓GSK3B, HDL, ↓HEXIM1, ↑LRPAP1, ↓MAP2, ↓MAPK1, ↑MYLK2, Myosin Light Chain Kinase, NGF, ↑PLIN2, PP1 protein complex group, ↑PPAT, Ppp2c, ↑PRDX3, ↑PRKAA2, ↓RPS6KA6, Rsk, ↓SERPINE2, Sfk, ↑SLC2A1, VLDL, ↓VLDLR | 27 | 18 | Cellular Assembly and Organization, Cellular Response to Therapeutics, Connective Tissue Development and Function |
| 6 | 26s Proteasome, Actin, Caspase, Cbp/p300, ↓CCNA2, ↑CCND1, Collagen type I, ↓CPSF6, ↓DHX9, ERK, F Actin, Histone h4, Holo RNA polymerase II, ↑IGFBP7, Insulin, Jnk, Lh, ↓MARCKS*, ↓MPRIP, ↓NOTCH1, ↓PDCD6IP, PI3K, Pkc(s), ↓PLXNA2, ↓PSIP1*, ↓PTP4A1, ↓RAD18, Rock, ↓SMC2, ↓SMC5, ↑TCEB1, ↑TCEB2, ↑UBE2C, Ubiquitin, Vegf | 27 | 18 | Cancer, Cellular Development, Cellular Growth and Proliferation |

Using the database DAVID that is offered for free by the National Institute of Allergy and Infectious Diseases (NIAID), annotation information was analyzed (for a detailed analysis method, see Nature Protocols 2009; 4(1): & Genome Biology 2003; 4(5), etc.). As a result of this analysis, it was found that a group of genes having similar biological functions, which are contained in large quantities in the genes of group 1 obtained as a result of the above-described microarray data analysis, are classified as clusters, and that these clusters are displayed in the order of clusters having high scores. It is determined that $p<0.05$ is statistically significant. As shown in the following Table 3, it was found that, in particular, genes relevant to cytoskeleton, such as those relevant to microtubule cytoskeleton or microtubule cytoskeleton organization, are contained in large quantities.

TABLE 3

| Annotation Cluster 18 | | Enrichment Score: 1.25 | G | | Count | P_Value | Benjamini |
|---|---|---|---|---|---|---|---|
| GOTERM_CC_FAT | | microtubule cytoskeleton | RT | | 13 | 3.0E−2 | 5.4E−1 |
| SP_PIR_KEYWORDS | | cytoskeleton | RT | | 11 | 3.9E−2 | 3.7E−1 |
| GOTERM_CC_FAT | | cytoskeleton | RT | | 24 | 6.1E−2 | 6.5E−1 |

TABLE 3-continued

| | | | | | | |
|---|---|---|---|---|---|---|
| GOTERM_CC_FAT | intracellular non-membrane-bounded organelle | RT | | 41 | 6.8E−2 | 6.6E−1 |
| GOTERM_CC_FAT | non-membrane-bounded organelle | RT | | 41 | 6.8E−2 | 6.6E−1 |
| GOTERM_CC_FAT | cytoskeletal part | RT | | 18 | 9.9E−2 | 6.6E−1 |
| Annotation Cluster 19 | Enrichment Score: 1.19 | G | | Count | P_Value | Benjamini |
| GOTERM_MF_FAT | protein methyltransferase activity | RT | | 4 | 2.7E−2 | 3.8E−1 |
| GOTERM_MF_FAT | histone methyltransferase activity | RT | | 3 | 7.2E−2 | 6.3E−1 |
| GOTERM_MF_FAT | N-methyltransferase activity | RT | | 3 | 1.4E−1 | 8.1E−1 |
| Annotation Cluster 20 | Enrichment Score: 1.18 | G | | Count | P_Value | Benjamini |
| GOTERM_BP_FAT | microtubule cytoskeleton organization | RT | | 6 | 3.6E−2 | 5.4E−1 |
| GOTERM_BP_FAT | cytoskeleton organization | RT | | 11 | 5.9E−2 | 6.5E−1 |
| GOTERM_BP_FAT | microtubule-based process | RT | | 7 | 1.4E−1 | 8.1E−1 |
| Annotation Cluster 21 | Enrichment Score: 1.15 | G | | Count | P_Value | Benjamini |

In Table 4 and Table 5 as shown below, 13 genes relevant to GOTERM_CC_FAT (microtubule cytoskeleton) and 6 genes relevant to GO_TERM_BP_FAT (microtubule cytoskeleton organization) are listed as clusters which were each determined to have a significant difference in the above Table 3 and comprise genes relevant to cytoskeleton. The probe set ID used in the above-described microarray test using the Affymetrix system was converted to UniGene ID, and the gene symbols of the genes with altered expression became clear.

molecule thereof, and is considered to be important for the development of a central nervous system, the movement or adhesion of cells, neurosecretion, and the like (Arbuzova et al., Biochem J. 2002, 362, 1-12). On the other hand, MAP2 (microtubule-associated protein 2) known as a microtubule-binding protein is found abundantly in cytoskeleton components. This protein acts as a substrate for many protein kinases or phosphatases, and is considered to regulate the relationship with cytoskeleton (Prog Neurobiol. 2000). Further, KIF5C was confirmed to be highly expressed in the lower motor

TABLE 4

GOTERM_CC_FAT
ID          GO:15630
Name        microtubule cytoskeleton
Ontology    Cellular Component
Definition  The part of the cytoskeleton (the internal framework of a cell) composed of microtubules and associated proteins.
Count       13
P_Value     3.00E−02
Benjamini   5.40E−01

List of genes with altered expression

| ProbeSetID | Representative_Public_ID | UniGeneID | EntrezGene | GeneSymbol |
|---|---|---|---|---|
| 1370949_at | M59859 | Rn.9560 | 25603///294446///681252 | LOC294446///LOC681252///Marcks |
| 1374299_at | BF398414 | Rn.107359 | 304859 | Dhx9 |
| 1388152_at | BG374290 | Rn.10484 | 25595 | Map2 |
| 1370948_a_at | M59859 | Rn.9560 | 25603///294446///681252 | LOC294446///LOC691252///Marcks |
| 1380172_at | BE104278 | Rn.50843 | 311024 | Kif5c |
| 1384213_at | AA955944 | Rn.101381 | 501083 | Pdcd6ip |
| 1383091_at | BE113611 | Rn.104856 | 303396 | Appbp2 |
| 1372102_at | BF390024 | Rn.24948 | 54299 | Ncor1 |
| 1373555_at | BM392315 | Rn.165969 | — | |
| 1370193_at | AI172261 | Rn.9459 | 29463 | Ptp4a1 |
| 1388185_at | AI178012 | Rn.55115 | 24708 | Rb1 |
| 1389190_at | BM392076 | Rn.23951 | 365468 | Lzts2 |
| 1370527_a_at | L07578 | Rn.8046 | 64462 | Csnk1d |
| 1389715_at | BI295883 | — | 292105 | Cep27l |

Among the above-described genes whose altered expression had been confirmed, MARCKS is a protein known as a main substrate for protein kinase C (PKC). This protein has a multiple binding domain interacting with a membrane lipid or a molecule such as calmodulin or actin, in the center of the neurons of mice that were 2 weeks old after birth or older, and thus, it was suggested that this protein should be necessary for the maintenance of motor neurons, rather than for formation of motor neurons (Kanai et al., The Journal of Neuroscience, 2000, 20(17): 6374-6384).

TABLE 5

GOTERM_BP_FAT
ID          GO:0000226
Name        microtubule cytoskeleton organization
Ontology    Biological Process
Definition  A process that is carried out at the cellular level which results in the assembly, arrangement of constituent parts, or disassembly of cytoskeletal structures comprising microtubules and their associated proteins
Count       6
P_Value     3.60E-02
Benjamini   540E-01

List of genes with altered expression

| ProbeSetID | Representative_Public_ID | UniGeneID | EntrezGene | GeneSymbol |
|---|---|---|---|---|
| 1388152_at | BG374290 | Rn.10484 | 25595 | Map2 |
| 1372015_at | AI008689 | Rn.73645 | 306582 | Tacc1 |
| 1372102_at | BF390024 | Rn.24948 | 54298 | Ncor1 |
| 1387875_at | BI294798 | Rn.2809 | 25614 | Ptk2 |
| 1380824_at | AI501458 | Rn.203282 | 306548 | Hook3 |
| 1389716_at | BI295883 | — | 292105 | Cep27I |

Among the above-described genes whose altered expression had been confirmed, MAP2, for example, is found abundantly in cytoskeleton components. This protein acts as a substrate for many protein kinases or phosphatases, and is considered to regulate the relationship with cytoskeleton (Prog Neurobiol. 2000).

[Results and Consideration]

As described above, genes whose expression had been altered by addition of the NAD analogue of the present invention were extracted, and they were then analyzed by IPA. As a result, as shown in the above Table 4 and Table 5, it was confirmed that in the nerve cells 24 hours after culture, a plurality of genes supporting the morphological alteration of cells were expressed more significantly than a control culture (the NAD analogue of the present invention). Accordingly, it was confirmed by molecular biological analysis that the NAD analogue of the present invention has an action to alter the shape of a central nerve cell, such as an action to allow neurites to elongate from the cell; namely, an ability to induce the differentiation of such central nerve cells. It was revealed that the NAD analogue of the present invention allows dopaminergic cells to differentiate. This suggests that the NAD analogue of the present invention can be utilized for and/or applied to the improvement of Parkinson's disease caused by the abnormality of dopaminergic cells, or depression whose relation with the NAD analogue has been pointed out.

Example 5

Effects of the NAD Analogue of the Present Invention on Various Types of Cells

The effects of the NAD analogue of the present invention on the cultured cells as described below weres studied. Human neuroblastoma-derived cells (NB-1 cells) and human myeloid leukemia cells (HL-60 cells) were purchased from RIKEN, Incorporated Administrative Agency. Human fibrosarcoma cells (HT1080 cells) and human colon-adenocarcinoma cells (HT29 cells) were purchased from Dainippon Sumitomo Pharma Co., Ltd. In addition, retinoic acid-resistant leukemia cells (UF-1 cells) were allocated from Dr. Masahiro KIZAKI at Keio University. These cells were cultured at 37° C. in the presence of 5% $CO_2$.

[Effect of the NAD Analogue of the Present Invention to Allow Neurites to Elongate from Human Neuroblastoma-Derived Cells (NB-1 Cells)]

The number of human neuroblastoma-derived cells (NB-cells), which were to be used as model cells for studying neurite outgrowth effect, was adjusted to $10^6$ cells/mL. Thus prepared NB-1 cells were cultured in an Eagle's MEM medium, to which calf serum had been added to a final concentration of 10% and to which 10 μg/mL of the NAD analogue of the present invention had also been added. After 7 days passed, the morphological alteration of the cells was observed under a phase-contrast microscope at a magnification of 200 times. The results are shown in FIG. 16.

[Results]

As is clear from FIG. 16B, it was observed that neurite-like structures elongated more significantly from NB-1 cells cultured in a medium to which the NAD analogue of the present invention had been added, than from the cells cultured in a medium to which the NAD analogue of the present invention had not been added (FIG. 16A). Accordingly, it became clear that the NAD analogue of the present invention has a promoting action on the outgrowth of neurites from nerve cells.

[Growth Suppressing Effect of the NAD Analogue of the Present Invention on Human Myeloid Leukemia Cells (HL-60 Cells)]

The number of human myeloid leukemia cells (HL-60 cells) was adjusted to $1.0×10^4$ cells/mL. The thus prepared HL-60 cells were cultured in an Eagle's MEM medium, to which calf serum had been added to a final concentration of 10% and to which the NAD analogue of the present invention had also been added in various concentrations of 0, 2.0, 4.0, and 8.0 μg/mL. After 5 days passed, the number of cells was counted. The results are shown in FIG. 17.

[Results]

Analysis was carried out by a t-test. It was determined that $p<0.05$ indicated a significant difference. As a result, it was found that when the NAD analogue of the present invention was added in an amount of 2.0 μg/mL or higher, the growth of the HL-60 cells was obviously suppressed in the concentration range of 2.0 μg/mL to 8.0 μg/mL (see FIG. 17).

[Apoptosis Induction of Human Myeloid Leukemia Cells (HL-60 Cells)]

Figure 18:
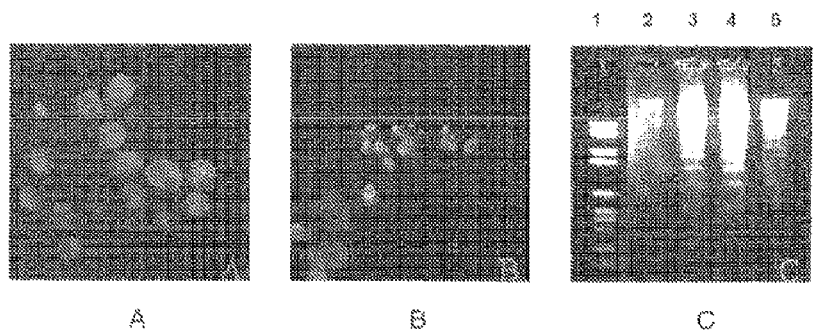
FIG. 18 This figure shows that HL-60 cells were induced to apoptosis by the NAD analogue of the present invention (FIG. 18B) and the results obtained by performing electrophoresis on DNA extracted from the cultured HL-60 cells (FIG. 18C).

The number of human myeloid leukemia cells (HL-60 cells) was adjusted to $1.0 \times 10^4$ cells/mL. The thus prepared HL-60 cells were cultured in an RPMI medium, to which calf serum had been added to a final concentration of 10% and to which the NAD analogue of the present invention had also been added in a concentration of 10 μg/mL or 20 μg/mL. Four days later, the cells were subjected to nuclear staining, and they were then observed under a fluorescence microscope. The results are shown in FIG. 18B. Furthermore, DNA was extracted from the cells according to an ordinary method and was then electrophoresed. The results are shown in FIG. 18C.
(Results)

In FIG. 18A, the shape of the nucleus in the HL-60 cell did not change in the case of the control to which the NAD analogue of the present invention had not been added. In contrast, in FIG. 18B, the breakage of the nucleus in the HL-60 cell was clearly observed in the case of culturing the HL-60 cells for 4 days in a medium to which the NAD analogue of the present invention had been added. This phenomenon shows that the cells were induced to apoptosis. FIG. 18C shows the results obtained by performing electrophoresis on DNA extracted from the HL-60 cells. Lane 1 shows a molecular size marker; lane 2 shows a control; and lanes 3 and 4 show the results obtained by performing electrophoresis on DNA extracted from the cells that were cultured in a medium, to which the NAD analogue of the present invention had been added in a concentration of 10 μg/mL or 20 μg/mL, respectively. In these lanes, fragmentation of the DNA due to apoptosis was observed in the form of a "ladder." Lane 5 shows a positive control, in which DNA extracted from the HL-60 cells cultured in a medium containing actinomycin D used as an anticancer agent was electrophoresed. These results demonstrate that the NAD analogue of the present invention induces apoptosis of HL-60 cells.

[Effect of the NAD Analogue of the Present Invention to Suppress Growth of Retinoic Acid-Resistant Leukemia Cells (UF-1 Cells)]

Figure 19:
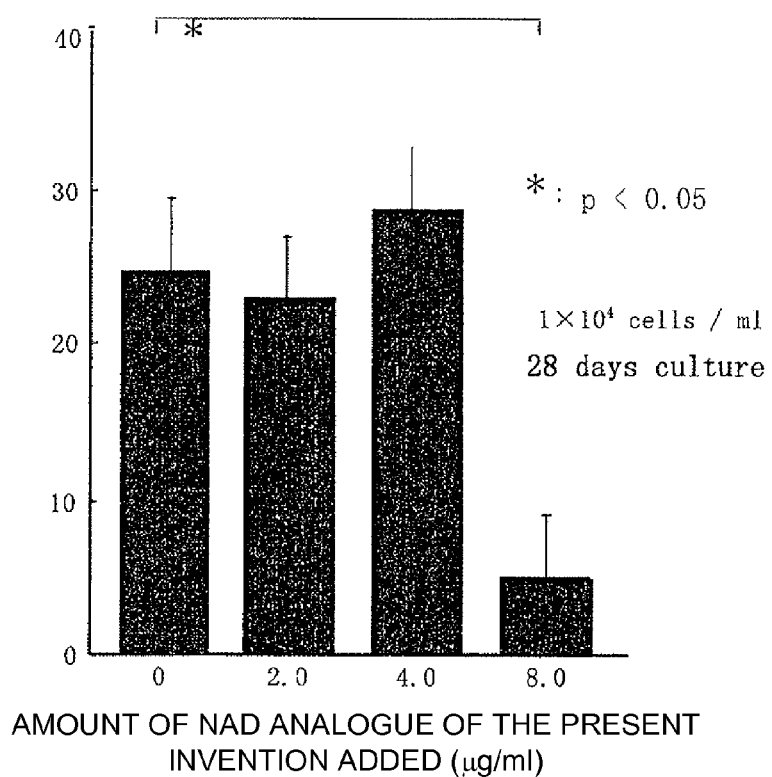
FIG. 19 This figure shows the effect of the NAD analogue of the present invention to suppress the growth of retinoic acid-resistant leukemia cells (UF-1 cells).

The number of retinoic acid-resistant leukemia cells (UF-1 cells) was adjusted to $1.0 \times 10^4$ cells/mL. The thus prepared UF-1 cells were cultured in an RPMI medium, to which calf serum had been added to a final concentration of 10% and to which the NAD analogue of the present invention had also been added in various concentrations of 0, 2.0, 4.0, and 8.0 μg/mL. After 28 days passed, the number of cells was counted. The results are shown in FIG. 19.
(Results)

Analysis was carried out by a t-test. It was determined that $p<0.05$ indicated a significant difference. As a result, it was found that when the NAD analogue of the present invention was added in an amount of 8.0 μg/mL or higher, the growth of the UF-1 cells was significantly suppressed. Thus, it was confirmed that the NAD analogue of the present invention apparently showed growth inhibitory effects on the cells (see FIG. 19). A differentiation induction therapy using retinoic acid has conventionally been carried out for the treatment of myeloid leukemia cells. It has been known that the leukemia cells eventually become resistant to retinoic acid, and thus the effect of retinoic acid becomes deactivated. However, from the results of the test using the NAD analogue of the present invention, it was confirmed that the NAD analogue of the present invention has an action to suppress the growth of even leukemia cells, which have acquired resistance to retinoic acid. In general, cells are not cultured for such a long period of time. The above-mentioned results were epoch-making in the sense that they were found after the culture for 28 days. The results suggest that the NAD analogue of the present invention could be applied to the treatment of leukemia.
(Effect of the NAD Analogue of the Present Invention to Suppress Growth of Human Tumor Cells)
[Effect of the NAD Analogue of the Present Invention to Suppress Growth of Human Fibrosarcoma Cells (HT1080 Cells)]

Figure 20:
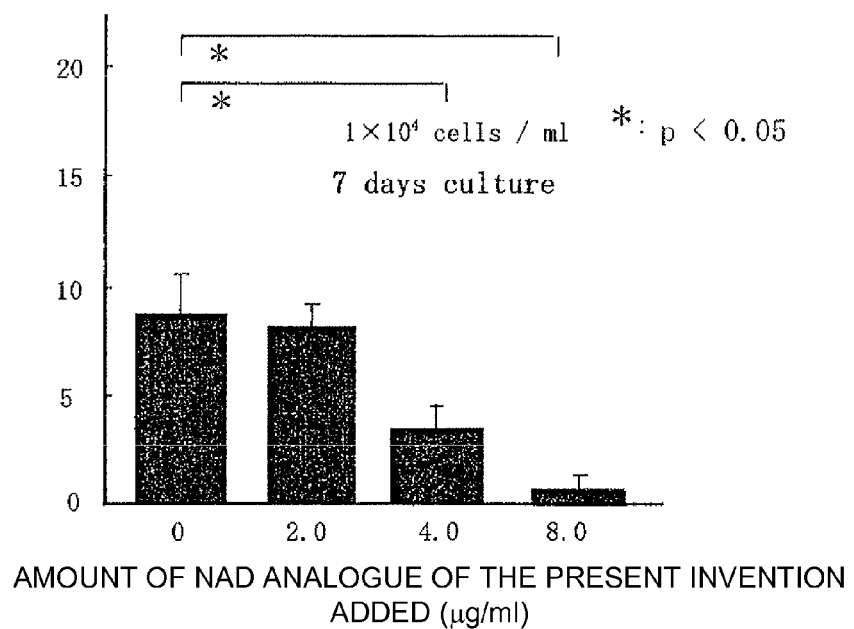
FIG. 20 This figure shows the effect of the NAD analogue of the present invention to suppress the growth of human fibrosarcoma cells (HT1080 cells).

The number of human fibrosarcoma cells (HT1080 cells) was adjusted to $1.0 \times 10^4$ cells/mL. Thus prepared HT1080 cells were cultured in an Eagle's MEM medium, to which calf serum had been added to a final concentration of 10% and to which the NAD analogue of the present invention had also been added in various concentrations of 0, 2.0, 4.0, and 8.0 μg/mL. After 7 days passed, the number of cells was counted. The results are shown in FIG. 20.

Analysis was carried out by a t-test. It was determined that $p<0.05$ indicated a significant difference. As a result, it was found that when the NAD analogue of the present invention was added in an amount of 4.0 μg/mL or higher, the growth of the cells was significantly suppressed (see FIG. 20).
[Effect of the NAD Analogue of the Present Invention to Suppress Growth of Human Colon-Adenocarcinoma Cells (HT29 Cells)]

Figure 21:
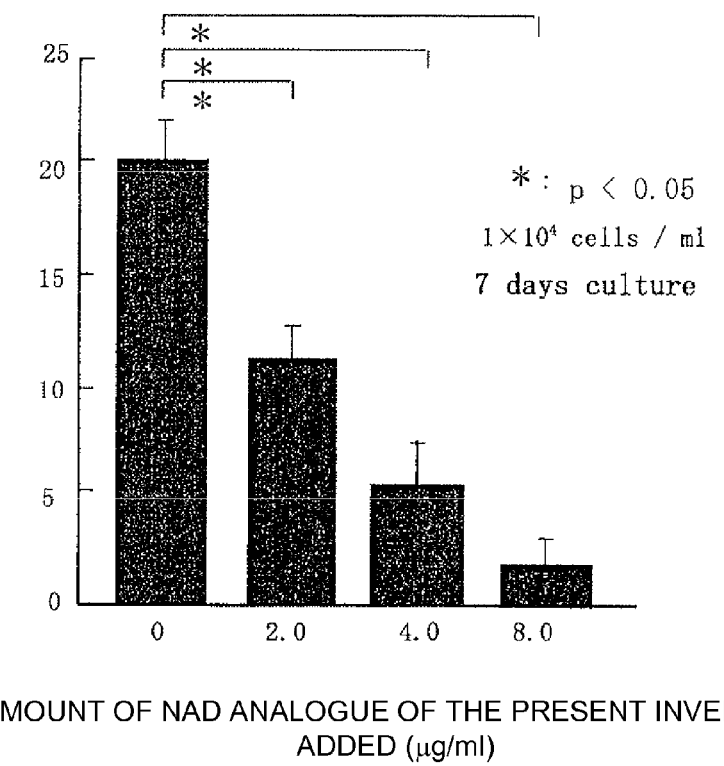
FIG. 21 This figure shows the effect of the NAD analogue of the present invention to suppress the growth of human colon-adenocarcinoma cells (HT29 cells).

The number of human colon-adenocarcinoma cells (HT29 cells) was adjusted to $1.0 \times 10^4$ cells/mL. Thus prepared HT29 cells were cultured in an Eagle's MEM medium, to which calf serum had been added to a final concentration of 10% and to which the NAD analogue of the present invention had also been added in various concentrations of 0, 2.0, 4.0, and 8.0 μg/mL. After 7 days passed, the number of cells was counted. The results are shown in FIG. 21.
(Results)

Analysis was carried out by a t-test. It was determined that $p<0.05$ indicated a significant difference. As a result, it was found that when the NAD analogue of the present invention was added in an amount of 2 μg/mL or higher, the growth of the cells was significantly suppressed (see FIG. 21). From the results obtained for HT1080 cells and HT29 cells, it was confirmed that the NAD analogue of the present invention showed growth inhibitory effects on tumor cells.

The invention claimed is:
1. A compound that is 3-(aminocarbonyl)-1-[5-O-[[1-(6-amino-9H-purin-9-yl)-1-deoxy-β-D-ribofuranose-5-O-yl]phosphonyloxy(oxylato)phosphinyl]-β-L-ribofuranosyl]pyridinium.

* * * * *

UNITED STATES PATENT AND TRADEMARK OFFICE
CERTIFICATE OF CORRECTION

PATENT NO.         : 8,481,711 B2
APPLICATION NO.    : 13/806933
DATED              : July 9, 2013
INVENTOR(S)        : Hidenori Kaminishi et al.

It is certified that error appears in the above-identified patent and that said Letters Patent is hereby corrected as shown below:

Title Page: Item 73

Please change the assignee information, (item 73) from: "Hidenori Kamanishi" to:
-- Hidenori Kaminishi --.

Signed and Sealed this
Third Day of November, 2015

Michelle K. Lee
*Director of the United States Patent and Trademark Office*